US009518014B2

(12) United States Patent
Ding et al.

(10) Patent No.: US 9,518,014 B2
(45) Date of Patent: Dec. 13, 2016

(54) PROCESS FOR SYNTHESIS OF EZETIMIBE AND INTERMEDIATES USED IN SAID PROCESS

(71) Applicant: SHANGHAI INSTITUTE OF ORGANIC CHEMISTRY, CHINESE ACADEMY OF SCIENCES, Xuhui District, Shanghai (CN)

(72) Inventors: Kuiling Ding, Shanghai (CN); Xiaoming Wang, Shanghai (CN); Zheng Wang, Shanghai (CN)

(73) Assignee: Shanghai Institute of Organic Chemistry, Chinese Academy of Sciences, Xuhui District, Shanghai (CN)

( * ) Notice: Subject to any disclaimer, the term of this patent is extended or adjusted under 35 U.S.C. 154(b) by 0 days.

(21) Appl. No.: 14/415,891

(22) PCT Filed: Jan. 29, 2013

(86) PCT No.: PCT/CN2013/071092
§ 371 (c)(1),
(2) Date: Jan. 20, 2015

(87) PCT Pub. No.: WO2014/012372
PCT Pub. Date: Jan. 23, 2014

(65) Prior Publication Data
US 2015/0166479 A1 Jun. 18, 2015

(30) Foreign Application Priority Data
Jul. 20, 2012 (CN) .......................... 2012 1 0253879

(51) Int. Cl.
| | | |
|---|---|---|
| C07C 229/34 | (2006.01) | |
| C07D 205/08 | (2006.01) | |
| C07D 205/04 | (2006.01) | |
| C07C 67/08 | (2006.01) | |
| C07C 68/00 | (2006.01) | |
| C07C 69/734 | (2006.01) | |
| C07C 69/96 | (2006.01) | |
| C07C 227/32 | (2006.01) | |
| C07C 227/16 | (2006.01) | |
| C07F 9/50 | (2006.01) | |
| C07F 15/00 | (2006.01) | |
| C07C 67/343 | (2006.01) | |
| C07C 67/31 | (2006.01) | |
| C07C 227/18 | (2006.01) | |
| C07C 229/30 | (2006.01) | |

(52) U.S. Cl.
CPC ............ *C07D 205/04* (2013.01); *C07C 67/08* (2013.01); *C07C 67/31* (2013.01); *C07C 67/343* (2013.01); *C07C 68/00* (2013.01); *C07C 69/734* (2013.01); *C07C 69/96* (2013.01); *C07C 227/16* (2013.01); *C07C 227/18* (2013.01); *C07C 227/32* (2013.01); *C07C 229/30* (2013.01); *C07C 229/34* (2013.01); *C07D 205/08* (2013.01); *C07F 9/5045* (2013.01); *C07F 15/0033* (2013.01); *C07C 2101/16* (2013.01)

(58) Field of Classification Search
None
See application file for complete search history.

(56) References Cited

U.S. PATENT DOCUMENTS 5,739,321 A 4/1998 Wu et al.
5,856,473 A 1/1999 Shankar

FOREIGN PATENT DOCUMENTS

| | | |
|---|---|---|
| CN | 102234246 A | 11/2011 |
| EP | 0720599 A1 | 7/1996 |
| EP | 1137634 B1 | 6/2005 |
| WO | 9508532 A1 | 3/1995 |

OTHER PUBLICATIONS

Wang, Xiaoming. Angew. Chem. Int. Ed. 51 (2012) 9276-9282.*
Int'l Search Report issued May 9, 2013 in Int'l Application No. PCT/CN2013/071092.
Lightfoot et al, "Enantioselective Hydrogenation of Olefins with Iridium—Phosphanodihydrooxazole Catalysts," Angew. Chem. Int. Ed., vol. 37, No. 20, pp. 2897-2899 (1998).
Han et al, "Sprio[4,4]-1,6-nonadiene-Based Phosphine-Oxazoline Ligands for Iridium-Catalyzed Enantioselective Hydrogenation of Ketimines," Angew. Chem. Int. Ed., vol. 48, pp. 5345-5349 (2009).
Sasikala et al, "An Improved and Scalable Process for the Synthesis of Ezetimibe: An Antihypercolesterolemia Drug," Organic Process Reseaerch & Development, vol. 13, pp. 907-910 (2009).
Sova et al, "(Z)-5-(4-Fluorophenyl)pent-4-enoic Acid: A Precursor for Convenient and Efficient Synthesis of the Antihypercholesterolemia Agent Ezetimibe," Synthesis, vol. 20, pp. 3433-3438 (2010).
Wu et al, "A Novel One-Step Diastereo- and Enantioselective Formation of trans-Azetidinones and Its Application to the Total Synthesis of Cholesterol Absorption Inhibitors," J. Org. Chem., vol. 64, pp. 3714-3718 (1999).

* cited by examiner

*Primary Examiner* — Golam M M Shameem
*Assistant Examiner* — Laura Daniel
(74) *Attorney, Agent, or Firm* — Panitch Schwarze Beliario & Nadel LLP

(57) ABSTRACT

A process for the production of ezetimibe and intermediates used in said process are disclosed. A kind of Morita-Baylis-Hillman adduct can be altered to chiral carboxylic acid derivatives of β-arylamino α-methylene with high activity and selectivity by means of ally lamination reaction, and the above carboxylic acid derivatives of β-arylamino α-methylene can be altered to the chiral intermediates of ezetimibe by means of simple conversion and further synthesized into the chiral drug ezetimibe. The synthesis route introduces chirality through the use of a chiral catalysis method, thereby avoiding the use of the chiral auxiliary oxazolidinone; and the route is economical and eco-friendly.

12 Claims, No Drawings

PROCESS FOR SYNTHESIS OF EZETIMIBE AND INTERMEDIATES USED IN SAID PROCESS

CROSS-REFERENCE TO RELATED APPLICATION

This application is a Section 371 of International Application No. PCT/CN2013/071092, filed Jan. 29, 2013, which was published in the Chinese language on Jan. 23, 2014, under International Publication No. WO 2014/012372 A1 the disclosure of which is incorporated herein by reference.

TECHNICAL FIELD

The invention relates to a synthetic method for Ezetimibe and intermediates used in said method.

BACKGROUND ART

Ezetimibe containing β-lactam structure is a novel cholesterol-lowering drug which was developed by Schering-Plough and approved for marketing by US Food and Drug Administration (FDA) at the end of 2002. It inhibits intestinal absorption of exogenous cholesterol to lower the concentrations of low density lipoprotein-cholesterol and total cholesterol in plasma. When it was used alone in clinic, it can lower low density lipoprotein-cholesterol (LDL-C) and significantly lower total cholesterol. The cholesterol-lowering effect obtained by Ezetimibe in combination with statins corresponds to that obtained by eight times of dose of statin.

EP720599 firstly disclosed the synthetic method for Ezetimibe:

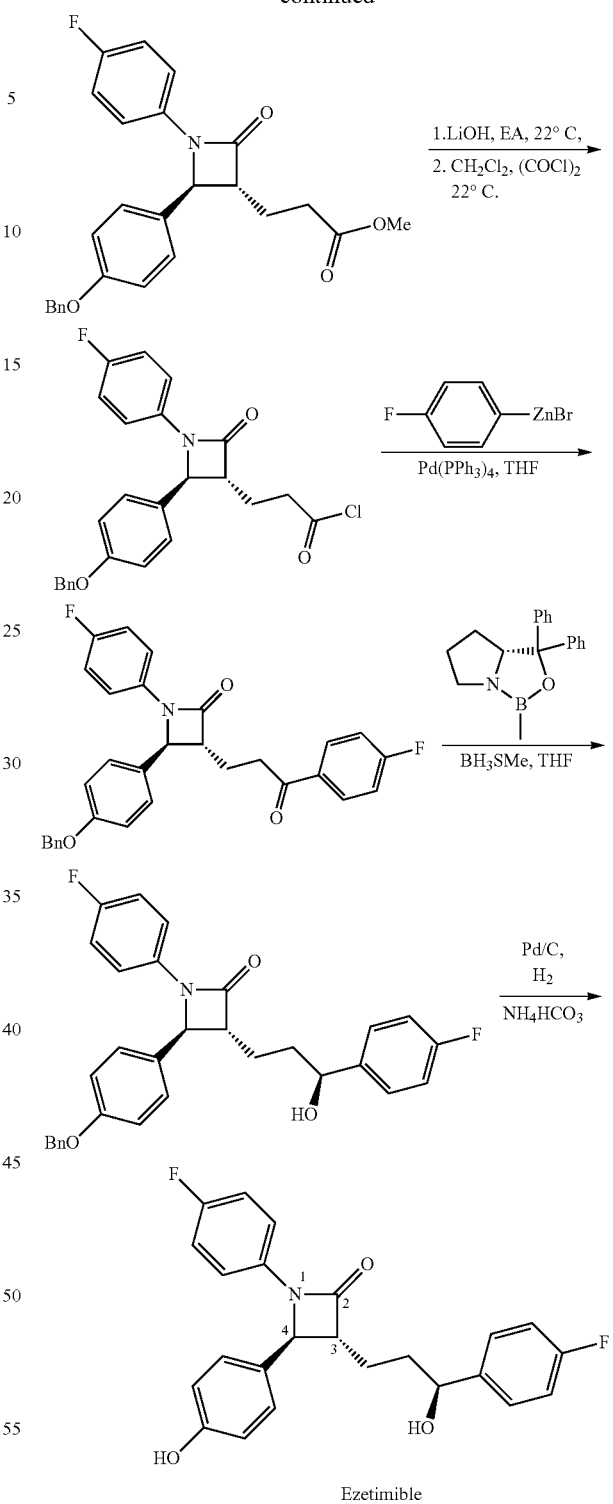

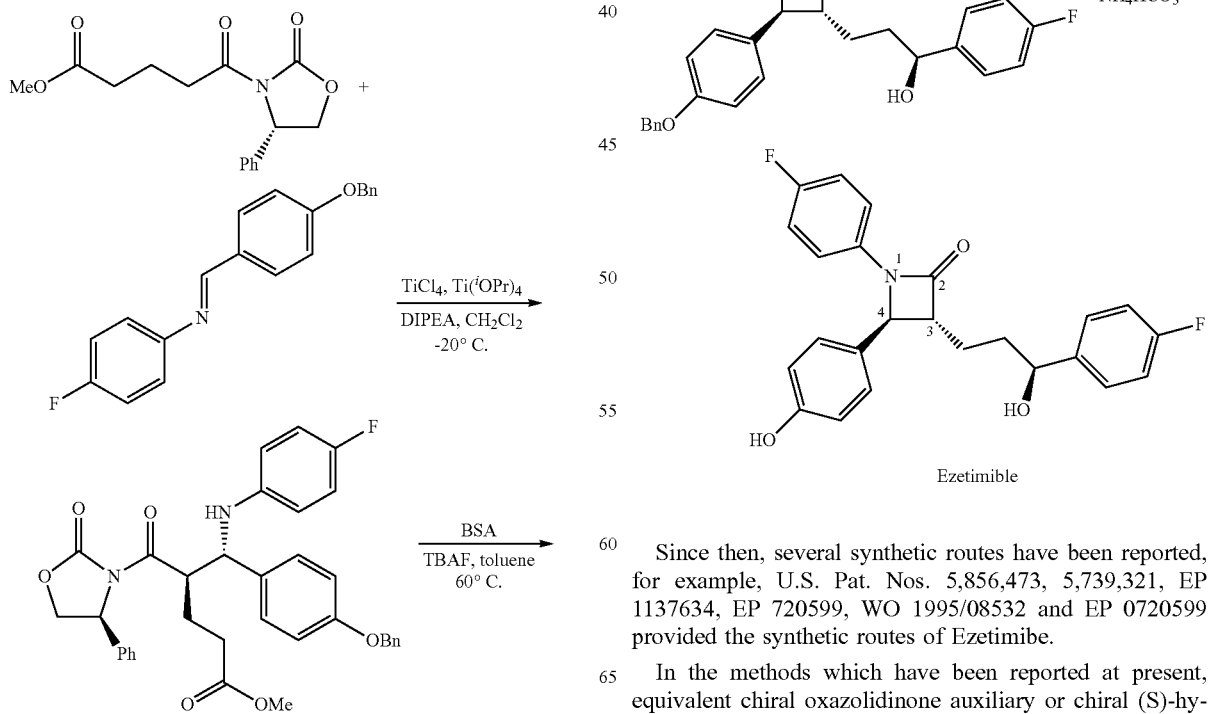

Since then, several synthetic routes have been reported, for example, U.S. Pat. Nos. 5,856,473, 5,739,321, EP 1137634, EP 720599, WO 1995/08532 and EP 0720599 provided the synthetic routes of Ezetimibe.

In the methods which have been reported at present, equivalent chiral oxazolidinone auxiliary or chiral (S)-hydroxy-butyrolactone was used as starting material for constructing key chiral C-4 in four-membered ring of lactam, which was not economic and environment-friendly and of high cost.

SUMMARY OF THE INVENTION

One object of the present invention is to provide a novel synthetic method for Ezetimibe and intermediates used in said method.

In the first aspect of the present invention, a compound of formula I is provided,

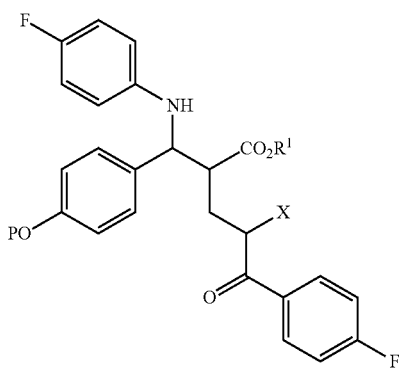

I wherein P is a hydrogen, an acetyl, a propionyl, a t-butyloxycarbonyl, a benzyl, a carbobenzoxy, a trityl, a trimethylsilyl, a tert-butyldimethylsilyl (TBS), a tert-butyldiphenylsilyl or a diphenylmethylsilyl;

$R^1$ is selected from the following group: a hydrogen, a methyl, an ethyl, an isopropyl, an n-butyl, a tert-butyl, a benzyl, an allyl or an adamantyl;

X is H or $CO_2R^2$; $R^2$ is selected from the following group: a hydrogen, a methyl, an ethyl, an isopropyl, an n-butyl, a tert-butyl, a benzyl, an allyl or an adamantly.

In another preferred embodiment, the compound of formula I is a compound of formula 4 or an enantiomer thereof,

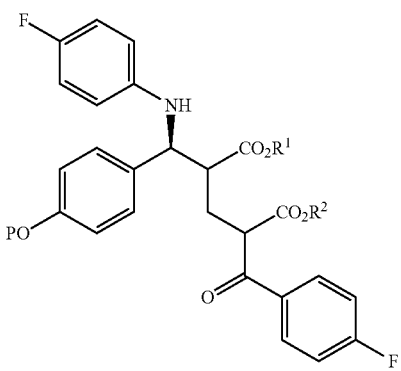

4 wherein, P, $R^1$, and $R^2$ are defined as above.

In another preferred embodiment, the compound of formula I is a compound of formula 5, or an enantiomer thereof

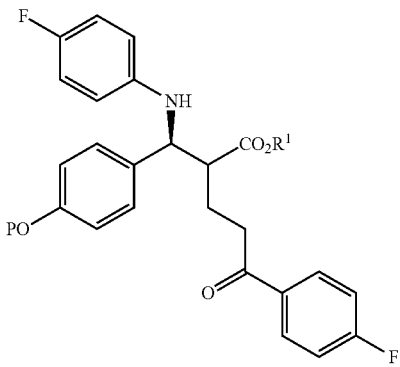

5 wherein, P, and $R^1$ are defined as above.

In the second aspect of the present invention, a preparation method for the compound of formula I is provided, comprising the following steps:

(a) a compound of formula 1 and p-fluoro aniline are subjected to an allyl amination reaction in the presence of a base to prepare a compound of formula 2;

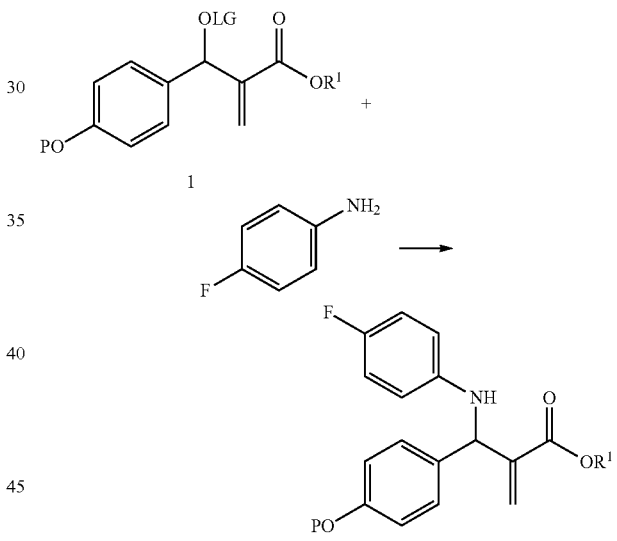

(b) the compound of formula 2 and a compound of formula 3 are subjected to an addition reaction under the action of a base to prepare the compound of formula I having a structure shown in formula 4A; and optionally,

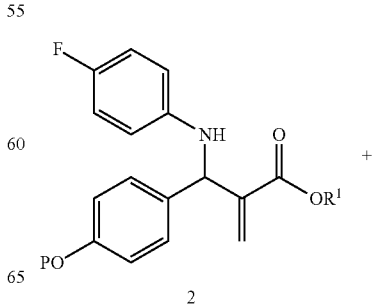

2

-continued

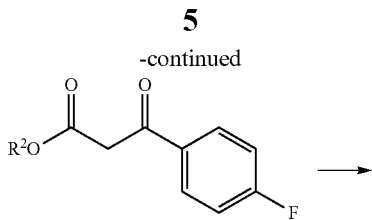

3

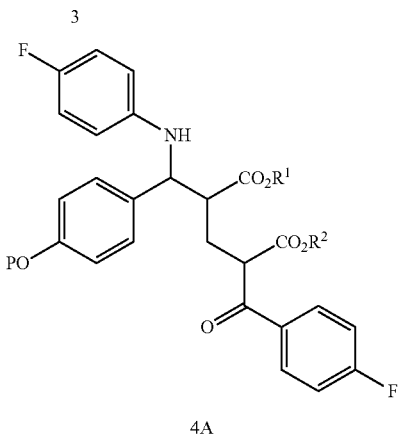

4A (c) an ester group at the β position of ketone carbonyl is removed from the compound of formula I having a structure shown in formula 4A to form the compound of formula I having a structure shown in formula 5A,

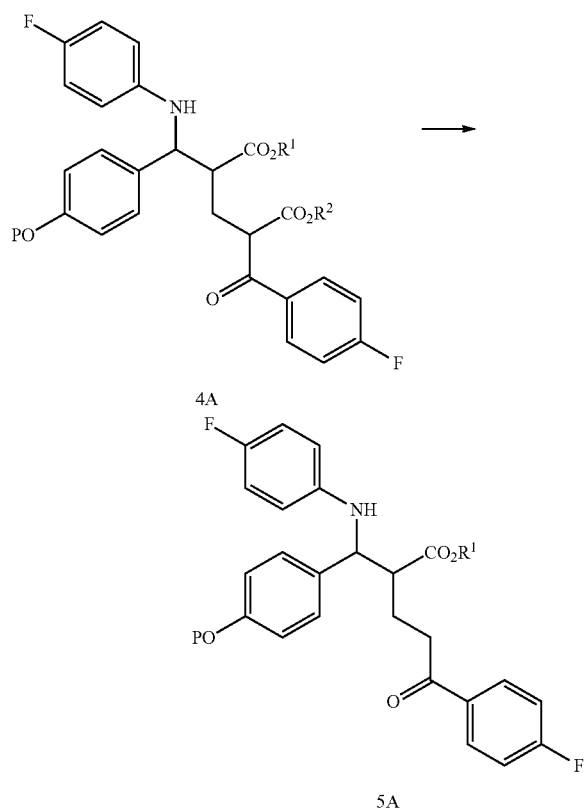

wherein P is a hydrogen, an acetyl, a propionyl, a t-butyloxycarbonyl, a benzyl, a carbobenzoxy, a trityl, a trimethylsilyl, a tert-butyldimethylsilyl, or diphenylmethylsilyl;

$R^1$ or $R^2$ independently is selected from the following group: a hydrogen, a methyl, an ethyl, an isopropyl, an n-butyl, a tert-butyl, a benzyl, an allyl or an adamantyl;

LG is selected from an acetyl (Ac), a t-butyloxycarbonyl (Boc), a methoxycarbonyl (—$CO_2$Me), a di(ethoxy)phosphinyl ($POEt_2$).

In another preferred embodiment, a complex which is formed from a phosphine ligand and a transition metal catalyst precursor is used as catalyst in step (a), wherein the phosphine ligand is

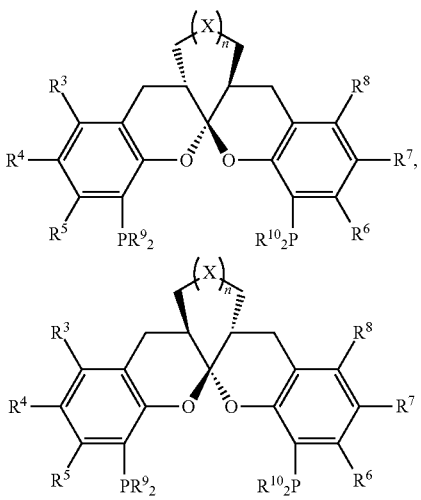

or a racemate containing both of them, wherein, $R^3$, $R^4$, $R^5$, $R^6$, $R^7$ and $R^8$ are independently and separately selected from a hydrogen, a halogen, a substituted or unsubstituted following group: a $C_1$-$C_{10}$ alkyl, a $C_1$-$C_4$ alkoxy, a $C_3$-$C_{30}$ cycloalkyl or an aryl; $R^9$ and $R^{10}$ are independently and separately selected from a $C_3$-$C_{10}$ cycloalkyl, a $C_1$-$C_{10}$ alkyl, a 2-furyl or an aryl; X is selected from $CH_2$, NH, $NCH_3$, O or S; n=0-4;

said substitution refers to be substituted by a substituent selected from the following group: a halogen, a $C_{1-6}$ alkyl, a $C_{1-6}$ haloalkyl or a $C_{1-6}$ alkoxy;

said transition metal catalyst precursor is a palladium catalyst precursor, and the palladium catalyst precursor is one or two or more than two selected from $Pd(OAc)_2$, $PdCl_2$, $Pd_2(dba)_3$, $Pd_2(dba)_3.CHCl_3$, $Pd(dba)_2$, $[Pd(C_3H_5)Cl]_2$, $Pd(PPh_3)_4$, $Pd(PPh_3)_2Cl_2$, $Pd(CH_3CN)Cl_2$. $Pd_2(dba)_3$ or $[Pd(C_3H_5)Cl]_2$ is preferred.

In another preferred embodiment, the base in step (a) is at least one selected from potassium carbonate, potassium phosphate, cesium carbonate, triethylamine, diisopropylethylamine, N,O-bis(trimethylsilyl)acetamide (BSA), and tetra-n-butylammonium difluorotriphenylsilicate (TBAT);

the base in step (b) is at least one selected from 1,8-diazabicyclo[5.4.0]undec-7-ene (DBU), 1,4-diazabicyclo[2.2.2]octane (BABCO), triethylamine, sodium hydroxide, potassium hydroxide, sodium hydride, potassium hydride, sodium ethoxide, and sodium methoxide.

In the third aspect of the present invention, a preparation method for a compound of formula 6A is provided, comprising subjecting the compound of formula I to a cyclization reaction under the action of a base to form the compound of formula 6A,

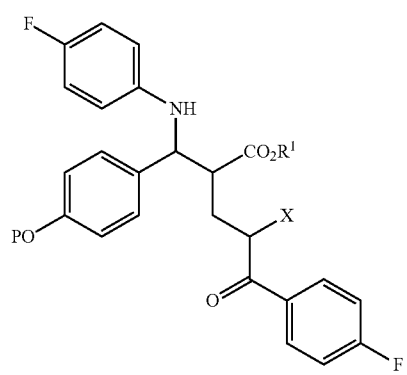

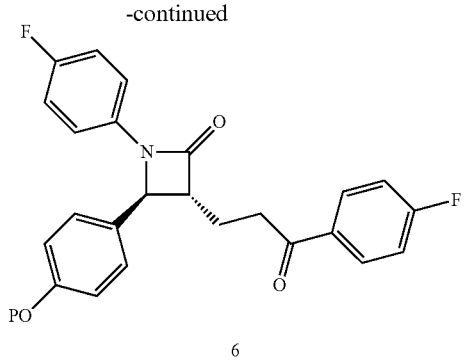

(i) a compound of formula 5 is subjected to a cyclization reaction under the action of a base to form a compound of formula 6;
(ii) the compound of formula 6 is subjected to asymmetric reduction reaction at the position of ketone carbonyl in an organic solvent to obtain a compound of formula 7;
(iii) a protection group is removed from the compound of formula 7 to obtain Ezetimibe, the compound of formula 8,

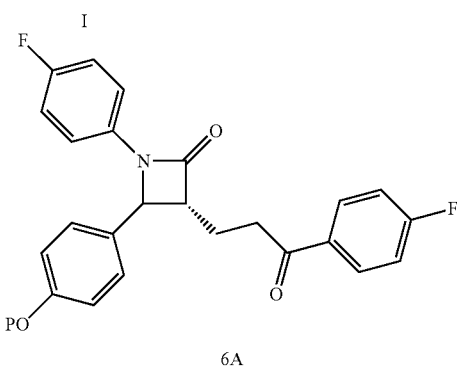

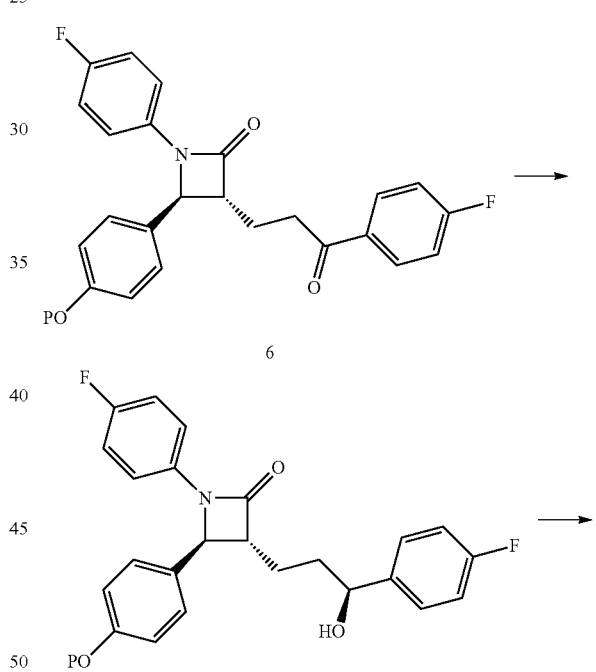

wherein P is a hydrogen, an acetyl, a propionyl, a t-butyloxycarbonyl, a benzyl, a carbobenzoxy, a trityl, a trimethylsilyl, a tert-butyldimethylsilyl or a diphenylmethylsilyl;

$R^1$ is selected from the following group: a hydrogen, a methyl, an ethyl, an isopropyl, an n-butyl, a tert-butyl, a benzyl, an allyl or an adamantyl;

X is H.

In another preferred embodiment, the base is at least one selected from Tin(II) bis-hexamethyldisilazide ($Sn[N(TMS)_2]_2$), lithium bis(trimethylsilyl)amide (LHMDS), lithium diisopropyl amide (LDA), butyl lithium, t-butyl lithium, t-butyl magnesium chloride, t-butyl bromide magnesium, isopropyl magnesium chloride, isopropyl magnesium bromide.

In the fourth aspect of the present invention, a preparation method for Ezetimibe, a compound of formula 8 is provided, comprising the following steps,

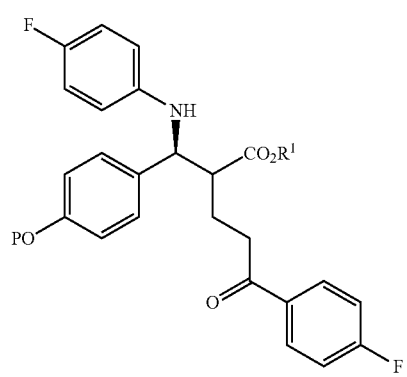

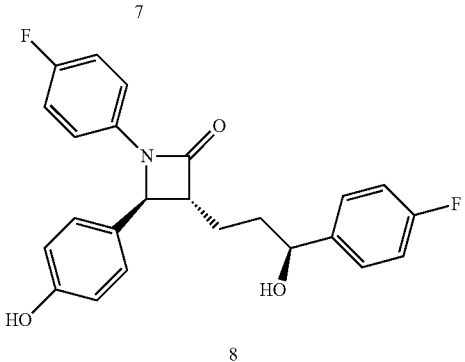

wherein P is a hydrogen, an acetyl, a propionyl, a t-butyloxycarbonyl, a benzyl, a carbobenzoxy, a trityl, a trimethylsilyl, a tert-butyldimethylsilyl or a diphenylmethylsilyl;

R¹ is selected from the following group: a hydrogen, a methyl, an ethyl, an isopropyl, an n-butyl, a tert-butyl, a benzyl, an allyl or an adamantly.

In another preferred embodiment, the base is at least one selected from Tin(II) bis-hexamethyldisilazide (Sn[N(TMS)₂]₂), lithium bis(trimethylsilyl)amide (LHMDS), lithium diisopropyl amide (LDA), butyl lithium, t-butyl lithium, t-butyl magnesium chloride, t-butyl bromide magnesium, isopropyl magnesium chloride, isopropyl magnesium bromide.

In another preferred embodiment, the organic solvent is at least one of benzene, toluene, xylene, dichloromethane, chloroform, carbon tetrachloride, 1,2-dichloroethane, diethyl ether, tetrahydrofuran, methanol, ethanol, N,N-dimethyl formamide or dimethyl sulfoxide.

In the fifth aspect of the present invention, a compound of formula II is provided,

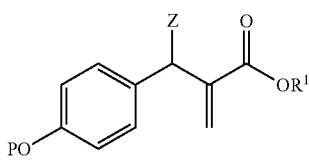

II wherein P is a hydrogen, an acetyl, a propionyl, a t-butyloxycarbonyl, a benzyl, a carbobenzoxy, a trityl, a trimethylsilyl, a tert-butyldimethylsilyl or a diphenylmethylsilyl;

R¹ is selected from the following group: a hydrogen, a methyl, an ethyl, an isopropyl, an n-butyl, a tert-butyl, a benzyl, an allyl or an adamantly;

Z is O-LG or

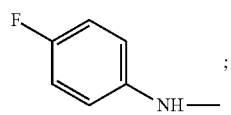

;

LG is selected from an acetyl (Ac), a t-butyloxycarbonyl (Boc), a methoxycarbonyl (—CO₂Me), a di(ethoxy)phosphinyl (POEt₂).

In another preferred embodiment, the compound is the compound of formula 1, the compound of formula 2 or an enantiomer of formula 2 compound,

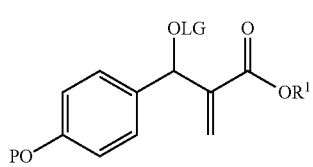

1

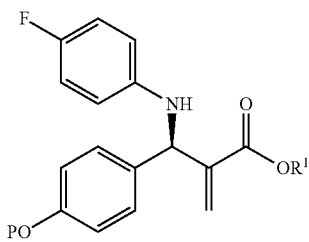

2 wherein P is a hydrogen, an acetyl, a propionyl, a t-butyloxycarbonyl, a benzyl, a carbobenzoxy, a trityl, a trimethylsilyl, a tert-butyldimethylsilyl or a diphenylmethylsilyl;

R¹ is selected from a hydrogen, a methyl, an ethyl, an isopropyl, an n-butyl, a tert-butyl, a benzyl, an allyl or an adamantyl;

LG is selected from the following group: an acetyl (Ac), a t-butyloxycarbonyl (Boc), a methoxycarbonyl (—CO₂Me), a di(ethoxy)phosphinyl (POEt₂).

In the sixth aspect of the present invention, a preparation method for the compound of formula 1 is provided, comprising the following step:

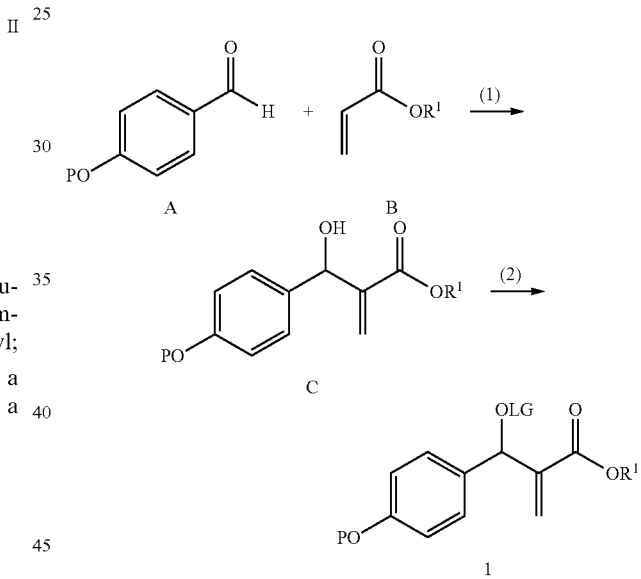

(1) a compound of formula A and a compound of formula B are subjected to Morita-Baylis-Hillman reaction to prepare a compound of formula C;

(2) a hydroxyl on the compound of formula C is protected to obtain the compound of formula 1, wherein P is a hydrogen, an acetyl, a propionyl, a t-butyloxycarbonyl, a benzyl, a carbobenzoxy, a trityl, a trimethylsilyl, a tert-butyldimethylsilyl, or diphenylmethylsilyl;

R¹ is selected from a hydrogen, a methyl, an ethyl, an isopropyl, an n-butyl, a tert-butyl, a benzyl, an allyl or an adamantyl;

LG is selected from the following group: an acetyl (Ac), a t-butyloxycarbonyl (Boc), a methoxycarbonyl (—CO₂Me), a di(ethoxy)phosphinyl (POEt₂).

In the present invention, a palladium-catalyzed asymmetric allylic amination was applied to the synthesises of Ezetimibe and intermediates thereof, thereby successfully avoiding the use of chiral auxiliary agents and achieving catalytic asymmetric construction of key chiral C-4 in Ezetimibe.

It should be understood that, within the scope of the present invention, the technical features specifically described above and below (such as the Examples) can be combined with each other, thereby constituting a new or preferred technical solution which needs not be described one by one.

SPECIFIC MODE FOR CARRYING OUT THE INVENTION

Upon extensive and in-depth research, the inventors prepared chiral aromatic spiroketal bisphosphine ligand and obtained Ezetimibe and intermediates thereof by using the ligand as catalysts, thereby successfully avoiding the use of chiral auxiliary agents as known in the art and achieving catalytic asymmetric construction of key chiral C-4 in Ezetimibe. Based on this, the present invention is accomplished.

Term

The term "alkyl" refers to a saturated linear or branched chain-hydrocarbon moiety, such as —CH$_3$ or —CH(CH$_3$)$_2$. The term "alkoxy" refers to a group generated from binding an alkyl and oxygen atom, such as —OCH$_3$, —OCH$_2$CH$_3$. The term "cycloalkyl" refers to a saturated cyclic hydrocarbon moiety, such as cyclohexyl. The term "aryl" means a hydrocarbon moiety containing one or more aromatic rings, including but not limited to phenyl, phenylene, naphthyl, naphthalene, pyrenyl, anthryl, phenanthryl and benzyl.

Unless otherwise specified, the alkyl, alkoxy, cycloalkyl and aryl described herein include substituted or unsubstituted moieties. Feasible substituents on the alkyl, alkoxy, cycloalkyl and aryl may include, but are not limited to: a $C_1$-$C_6$ alkyl, a $C_1$-$C_6$ haloalkyl, a $C_2$-$C_6$ alkenyl, a $C_2$-$C_6$ alkynyl, a $C_3$-$C_{10}$ cycloalkyl, a $C_3$-$C_{10}$ cycloalkenyl, a $C_1$-$C_6$ alkoxy, an aryl, a hydroxy, a halogen, an amino.

Compound of Formula II

As used herein, the compound of formula II, the compound II, the compound as shown in formula II and the compound shown in formula II have the same meaning and refer to the compound having the following structure:

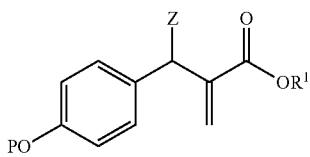

II wherein P is a hydrogen, an acetyl, a propionyl, a t-butyloxycarbonyl, a benzyl, a carbobenzoxy, a trityl, a trimethylsilyl, a tert-butyldimethylsilyl or a diphenylmethylsilyl;

R$^1$ is selected from the following group: a hydrogen, a methyl, an ethyl, an isopropyl, an n-butyl, a tert-butyl, a benzyl, an allyl and an adamantly;

Z is O-LG or

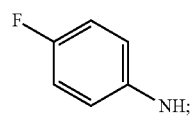

LG is selected from an acetyl (Ac), a t-butyloxycarbonyl (Boc), a methoxycarbonyl (—CO$_2$Me), a di(ethoxy)phosphinyl (POEt$_2$).

In another preferred embodiment, the compound of formula II is the compound of formula 1 or the compound of formula 2,

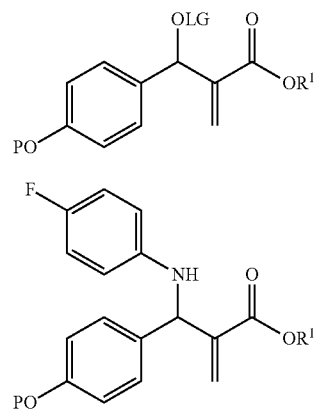

wherein P, R$^1$ and LG are defined as above.

The compound of Formula 2 according to the present invention can be a racemate, a compound of formula 2X or an enantiomer of the compound of formula 2X.

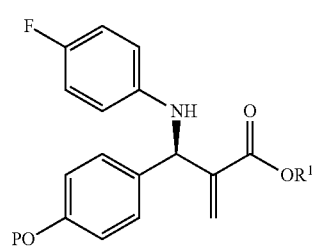

The compound of formula 1 can be prepared according to the following method in the present invention, comprising the steps of:

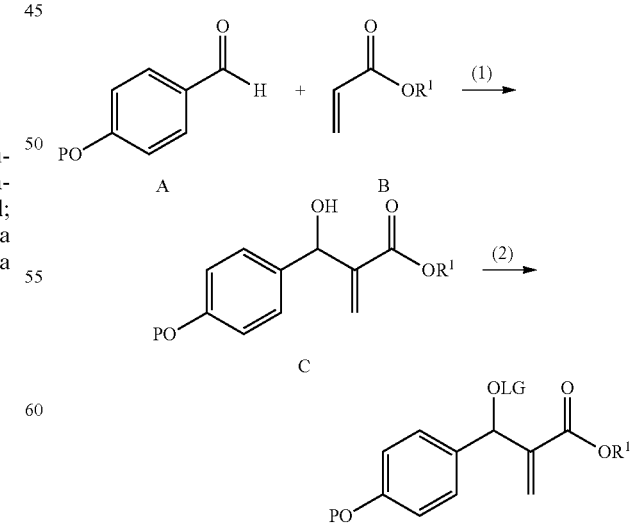

(1) the compound of formula A and the compound of formula B are subjected to Morita-Baylis-Hillman reaction to prepare the compound of formula C;

(2) a hydroxyl on the compound of formula C is protected to obtain the compound of formula 1, wherein P, $R^1$ and LG are defined as above.

In another preferred embodiment, in the presence of a base (such as tertiary amine or organic phosphine), the compound of formula C can be obtained by reacting the compound of formula A and the compound of formula B in a organic solvent or a mixed solvent of organic solvent and water or under solvent-free condition at 0-60° C. for 2 hr-15 days.

In another preferred embodiment, said organic solvent is at least one selected from the following group: benzene, toluene, xylene, dichloromethane, chloroform, carbon tetrachloride, 1,2-dichloroethane, diethyl ether, tetrahydrofuran, methanol, ethanol, N,N-dimethyl formamide and dimethyl sulfoxide.

In step (2), the hydroxyl on the compound of formula C can be protected according to conventional methods in the art.

The compound of formula 2 can be prepared according to the following method in the present invention, comprising the step of:

Subjecting the compound of formula 1 and p-fluoro aniline to an allyl amination reaction in the presence of a base to prepare the compound of formula 2;

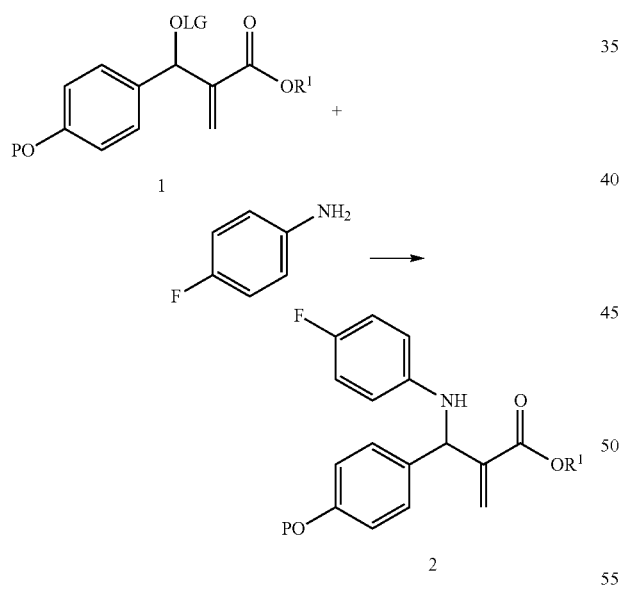

wherein P, $R^1$ and LG are defined as above.

The reaction can be carried out in a organic solvent. Said organic solvent is at least one, two or more selected from the following group: benzene, toluene, xylene, dichloromethane, chloroform, carbon tetrachloride, 1,2-dichloroethane, diethyl ether, tetrahydrofuran, methanol, ethanol, N,N-dimethyl formamide and dimethyl sulfoxide.

A complex which is formed from a phosphine ligand and a transition metal catalyst precursor can be used as catalyst in said reaction, the phosphine ligand is:

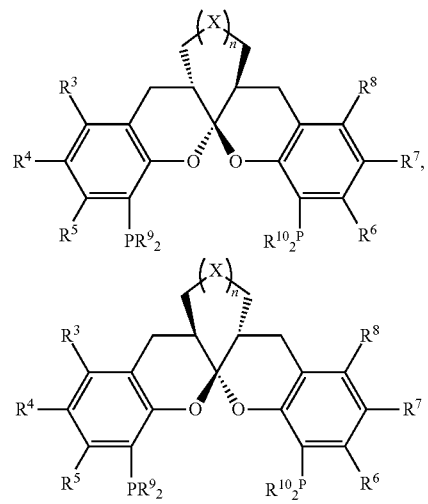

or a racemate containing both of them, wherein $R^3$, $R^4$, $R^5$, $R^6$, $R^7$ and $R^8$ are independently and separately selected from a hydrogen, a halogen, a substituted or unsubstituted following group: a $C_1$-$C_{10}$ alkyl, a $C_1$-$C_4$ alkoxy, a $C_3$-$C_{30}$ cycloalkyl or an aryl; $R^9$ and $R^{10}$ are independently and separately selected from a $C_3$-$C_{10}$ cycloalkyl, a $C_1$-$C_{10}$ alkyl, a 2-furyl or an aryl; X is selected from $CH_2$, NH, $NCH_3$, O or S; n=0-4;

said substitution refers to be substituted by a substituent which is selected from the following group: a halogen, a $C_{1-6}$ alkyl, a $C_{1-6}$ haloalkyl and a $C_{1-6}$ alkoxy;

said transition metal catalyst precursor is a palladium catalyst precursor, and the palladium catalyst precursor is one or two or more than two selected from $Pd(OAc)_2$, $PdCl_2$, $Pd_2(dba)_3$, $Pd_2(dba)_3 \cdot CHCl_3$, $Pd(dba)_2$, $[Pd(C_3H_5)Cl]_2$, $Pd(PPh_3)_4$, $Pd(PPh_3)_2Cl_2$, $Pd(CH_3CN)Cl_2$. $Pd_2(dba)_3$ or $[Pd(C_3H_5)Cl]_2$ is preferred.

Said substitution refers to mono-substituted, di-substituted, tri-substituted, or tetra-substituted, preferably, mono-substituted, di-substituted or tri-substituted.

In another preferred embodiment, a complex which is formed from

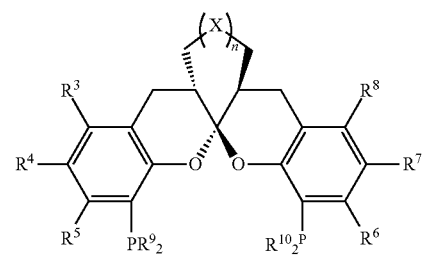

and a transition metal catalyst precursor is used as a catalyst to obtain the compound of formula 2X;

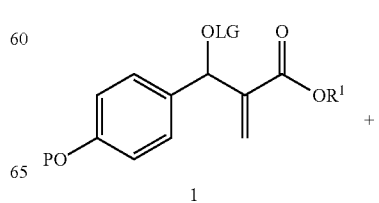

-continued

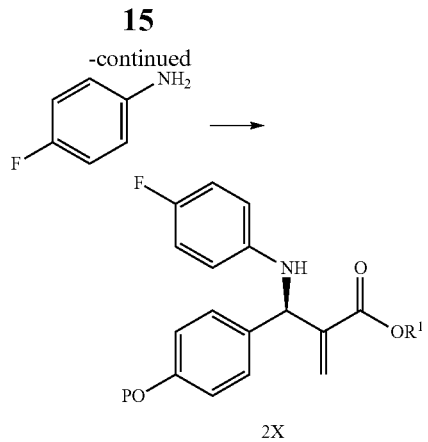

2X wherein P, R$^1$ and LG are defined as above.

In another preferred embodiment, a complex which is formed from

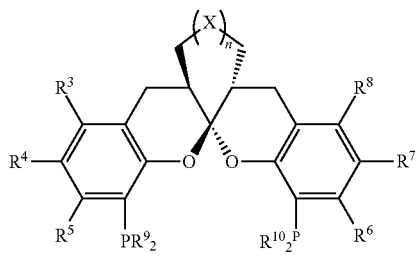

and a transition metal catalyst precursor is used as a catalyst to obtain an enantiomer of the compound of formula 2X.

In another preferred embodiment, a racemic phosphine ligand is used to obtain a racemic compound of formula 2.

The complex formed from a phosphine ligand and a transition metal catalyst precursor is obtained by reacting the chiral phosphine ligand and the transition metal catalyst precursor in an organic solvent under an inert atmosphere at −78° C.-100° C. for 0.1-1.0 hr. Said organic solvent is at least one selected from benzene, toluene, xylene, dichloromethane, chloroform, carbon tetrachloride, 1,2-dichloroethane, diethyl ether, tetrahydrofuran, methanol, ethanol, N,N-dimethyl formamide or dimethyl sulfoxide.

In another preferred embodiment, the mole ratio of said phosphine ligand, transition metal catalyst precursor to the compound of formula 1 is (1-10): 1: 50-10000.

Said base is at least one selected from the following group: potassium carbonate, potassium phosphate, cesium carbonate, triethylamine, diisopropylethylamine, N O-bis(trimethylsilyl)acetamide (BSA), tetrabutylammonium difluorotriphenylsilicate (TBAT). Said base can be dissolved in water for use. For example, 0.1-8.0 mol/L, preferably, 0.5-5 mol/L aqueous potassium carbonate solution can be used.

In another preferred embodiment, the base used in step (a) preferably is aqueous potassium carbonate solution (1-2 mol/L) or triethylamine In another preferred embodiment, the mole ratio of said base, p-fluoro aniline to the compound of formula I used in step (a) is 1-10: 1-10:1.

In another preferred embodiment, the reaction time of step (a) is 0.1-48 hr.

Compound of Formula I

As used herein, the compound of formula I, compound I, the compound as shown in formula I and the compound shown in formula I have the same meaning and refer to the compound having the following structure:

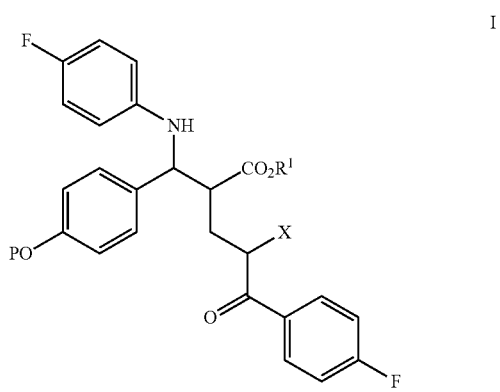

I wherein P is a hydrogen, an acetyl, a propionyl, a t-butyloxycarbonyl, a benzyl, a carbobenzoxy, a trityl, a trimethylsilyl, a tert-butyldimethylsilyl (TBS), a tert-butyldiphenylsilyl or a diphenylmethylsilyl;

R$^1$ is selected from the following group: a hydrogen, a methyl, an ethyl, an isopropyl, an n-butyl, a tert-butyl, a benzyl, an allyl or an adamantyl;

X is H or CO$_2$R$^2$; R$^2$ is selected from the following group: a hydrogen, a methyl, an ethyl, an isopropyl, an n-butyl, a tert-butyl, a benzyl, an allyl or an adamantly.

In another preferred embodiment, the compound of formula I is the compound of formula 4, or an enantiomer thereof,

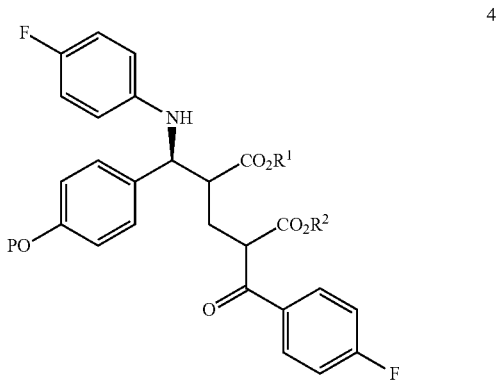

4 wherein P, R$^1$ and R$^2$ are defined as above.

In another preferred embodiment, the compound of formula I is the compound of formula 5, or an enantiomer thereof,

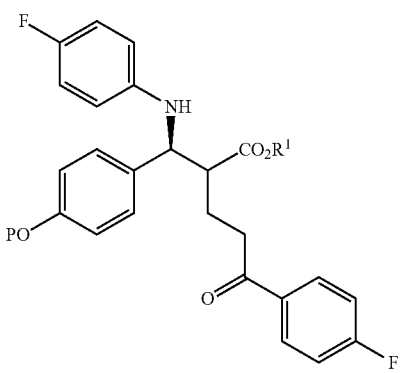

wherein P and R¹ are defined as above.

The preparation method of the compound of formula I in the present invention includes the following steps:

(a) the compound of formula 1 and p-fluoro aniline are subjected to an allyl amination reaction in the presence of a base to prepare the compound of formula 2;

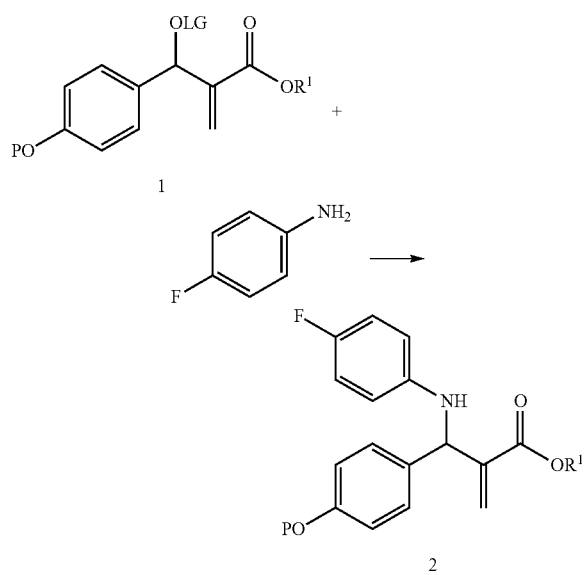

(b) the compound of formula 2 and the compound of formula 3 are subjected to an addition reaction under the action of a base to prepare the compound of formula I having a structure shown in formula 4A; and optionally,

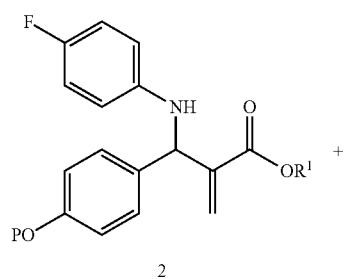

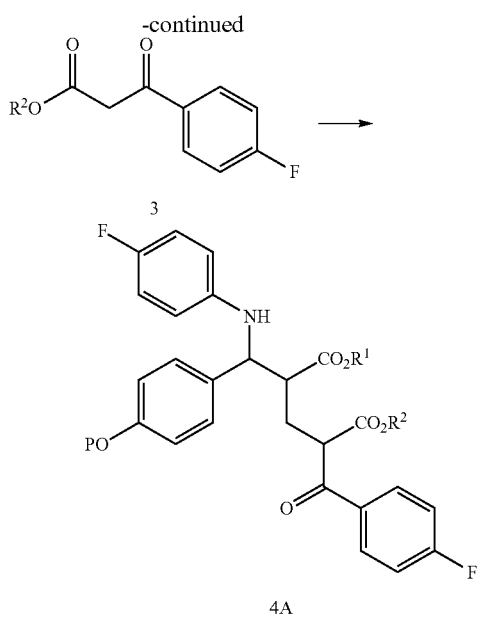

(c) an ester group at the β position of ketone carbonyl is removed from the compound of formula I having a structure shown in formula 4A to form the compound of formula I having a structure shown in formula 5A,

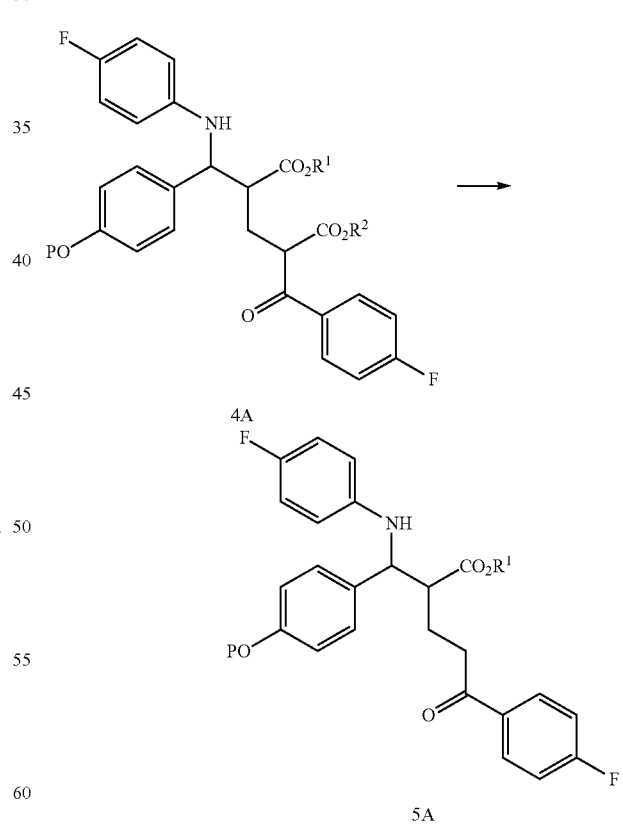

wherein P, R¹, R² and LG are defined as above.

In another preferred embodiment, a complex formed from a phosphine ligand and a transition metal catalyst precursor is used as a catalyst in step (a), the phosphine ligand is:

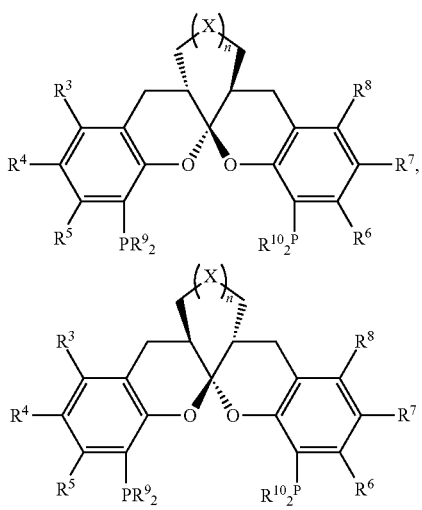

or a racemate containing both of them, wherein $R^3$, $R^4$, $R^5$, $R^6$, $R^7$ and $R^8$ are independently and separately selected from a hydrogen, a halogen, a substituted or unsubstituted following group: a $C_1$-$C_{10}$ alkyl, a $C_1$-$C_4$ alkoxy, a $C_3$-$C_{30}$ cycloalkyl or an aryl; $R^9$ and $R^{10}$ are independently and separately selected from a $C_3$-$C_{10}$ cycloalkyl, a $C_1$-$C_{10}$ alkyl, a 2-furyl or an aryl; X is selected from $CH_2$, NH, $NCH_3$, O or S; n=0-4;

said substitution refers to be substituted by a substituent which is selected from the following group: a halogen, a $C_{1-6}$ alkyl, a $C_{1-6}$ haloalkyl or a $C_{1-6}$ alkoxy;

said transition metal catalyst precursor is a palladium catalyst precursor, and the palladium catalyst precursor is one or two or more than two selected from the following group: $Pd(OAc)_2$, $PdCl_2$, $Pd_2(dba)_3$, $Pd_2(dba)_3.CHCl_3$, $Pd(dba)_2$, $[Pd(C_3H_5)Cl]_2$, $Pd(PPh_3)_4$, $Pd(PPh_3)_2Cl_2$, $Pd(CH_3CN)Cl_2$. $Pd_2(dba)_3$ or $[Pd(C_3H_5)Cl]_2$ is preferred.

In another preferred embodiment, the compound of formula 2X and the compound of formula 3 are subjected to addition reaction under the action of base to obtain the compound of formula 4,

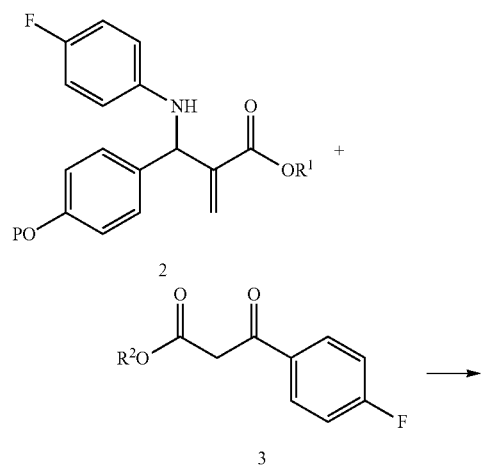

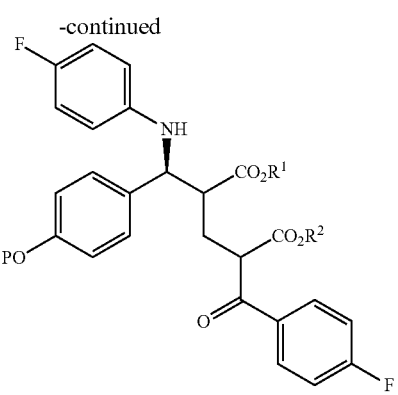

wherein P, $R^1$ and $R^2$ are defined as above.

In another preferred embodiment, the ester group at the β position of ketone carbonyl is removed from the compound of formula 4 to form the compound of formula 5,

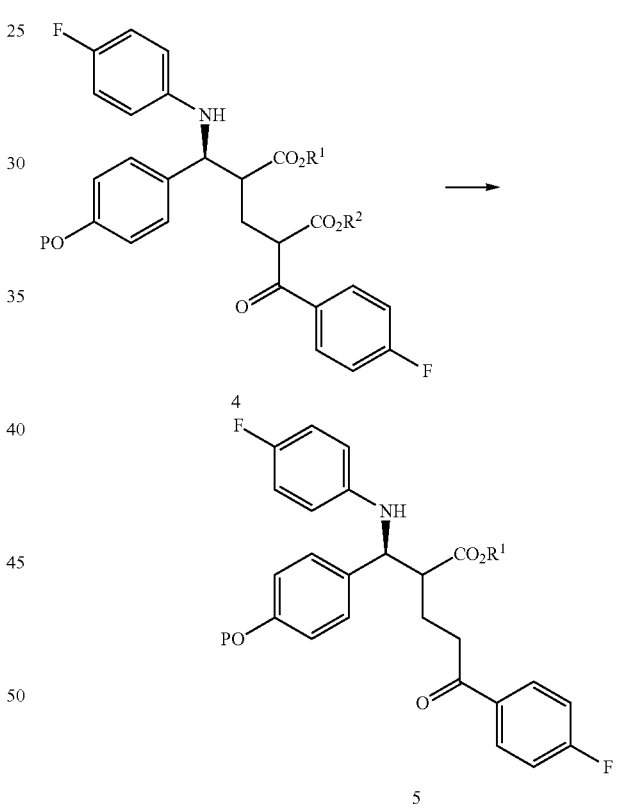

wherein P, $R^1$ and $R^2$ are defined as above.

In another preferred embodiment, said complex formed from a phosphine ligand and a transition metal catalyst precursor is obtained from the reaction of said chiral phosphine ligand and said transition metal catalyst precursor in an organic solvent under an inert atmosphere at −78° C.-100° C. for 0.1-1.0 hr. Said organic solvent is at least one selected from benzene, toluene, xylene, dichloromethane, chloroform, carbon tetrachloride, 1,2-dichloroethane, diethyl ether, tetrahydrofuran, methanol, ethanol, N,N-dimethyl formamide or dimethyl sulfoxide.

In another preferred embodiment, the mole ratio of said phosphine ligand, transition metal catalyst precursor to the compound of formula 1 is (1-10): 1: 50-10000.

In another preferred embodiment, the base used in step (a) is at least one selected from the following group: potassium carbonate, potassium phosphate, cesium carbonate, aqueous potassium carbonate solution (0.1-8.0 mol/L), triethylamine, diisopropylethylamine, N,O-bis(trimethylsilyl)acetamide (BSA), tetrabutylammonium difluorotriphenylsilicate (TBAT);

the base used in step (b) is at least one selected from the following group: 1,8-diazabicyclo[5.4.0]undec-7-ene (DBU), 1,4-diazabicyclo[2.2.2]octane (BABCO), triethylamine, sodium hydroxide, potassium hydroxide, sodium hydride, potassium hydride, sodium ethoxide, and sodium methoxide.

In another preferred embodiment, the base used in step (a) is an aqueous potassium carbonate solution (1-2 mol/L) or triethylamine.

In another preferred embodiment, the mole ratio of the base, p-fluoro aniline to the compound of formula 1 in step (a) is 1-10: 1-10:1.

In another preferred embodiment, the reaction time of step (a) is 0.1-48 hr.

In another preferred embodiment, the base used in step (b) is preferably 1,8-diazabicyclo[5.4.0]undec-7-ene (DBU).

In another preferred embodiment, the mole ratio of the compound of formula 3 to the compound of formula 2 is 1-10:1, preferably, 1.5-2:1.

In another preferred embodiment, the mole ratio of the base and the compound of formula 2 is 1-10:1, preferably, 2-3:1.

In another preferred embodiment, the reaction time of step (b) is 6-48 hr, preferably, 12-24 hr.

The compound of formula 4A can be directly used in de-esterification without being separated from the reaction system to form the compound of formula 5A. Alternatively, the compound of formula 4A can be separated and purified, and then used in de-esterification to form the compound of formula 5A.

In another preferred embodiment, when $R^2$ is Bn, Pd/C is used as a catalyst in step (c) and —$CO_2$Bn can be removed under hydrogen atmosphere.

In another preferred embodiment, when $R^2$ is an allyl, metal palladium salt (such as one, two or more than two selected from the following group: $Pd(OAc)_2$, $PdCl_2$, $Pd_2(dba)_3$, $Pd_2(dba)_3 \cdot CHCl_3$, $Pd(dba)_2$, $[Pd(C_3H_5)Cl]_2$, $Pd(PPh_3)_4$, $Pd(PPh_3)_2Cl_2$, $Pd(CH_3CN)Cl_2$; preferably $Pd_2(dba)_3$ or $[Pd(C_3H_5)Cl]_2$) is used as a catalyst in step (c) for removing allyl ester in the presence of an additive (such as morpholine, cyclohexylamine, dialkylamine or a mixture thereof).

In another preferred embodiment, when $R^2$ is methyl, —$CO_2$Me can be removed in step (c) in the presence of a base (such as sodium hydroxide, lithium hydroxide, potassium hydroxide, potassium carbonate, sodium carbonate, cesium carbonate or a mixture thereof) by heating.

Preparation Method for the Compound of Formula 6A

The present invention provides the preparation method for the compound of formula 6A, comprising subjecting the compound of formula I to a cyclization reaction under the action of a base to form the compound of formula 6A,

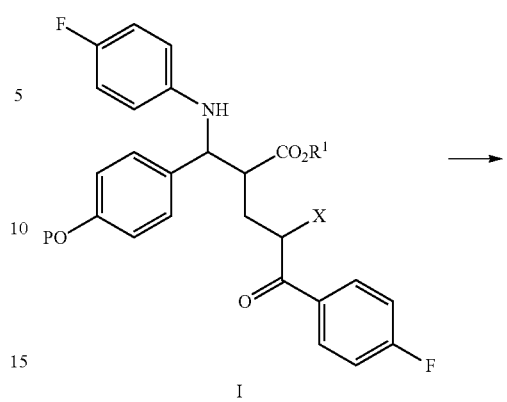

wherein P is a hydrogen, an acetyl, a propionyl, a t-butyloxycarbonyl, a benzyl, a carbobenzoxy, a trityl, a trimethylsilyl, a tert-butyldimethylsilyl or a diphenylmethylsilyl;

$R^1$ is selected from the following group: a hydrogen, a methyl, an ethyl, an isopropyl, an n-butyl, a tert-butyl, a benzyl, an allyl or an adamantly;

X is H.

In another preferred embodiment, the compound of formula 5 is subjected to a cyclization reaction under the action of a base to form the compound of formula 6,

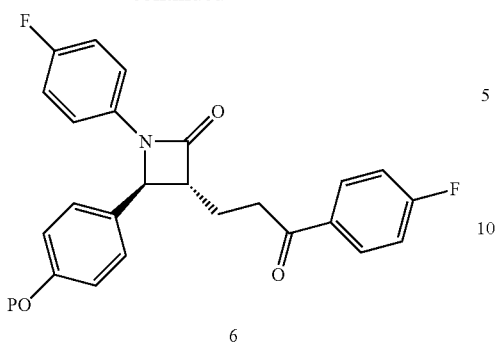

6 wherein P and R¹ are defined as above.

In another preferred embodiment, the base is at least one selected from Tin(II) bis-hexamethyldisilazide (Sn[N(TMS)₂]₂), lithium bis(trimethylsilyl)amide (LHMDS), lithium diisopropyl amide (LDA), butyl lithium, t-butyl lithium, t-butyl magnesium chloride, t-butyl bromide magnesium, isopropyl magnesium chloride, or isopropyl magnesium bromide.

In another preferred embodiment, the base is preferably lithium bis(trimethylsilyl)amide (LHMDS).

In another preferred embodiment, the mole ratio of the base to the compound of formula I (or the compound of formula 5) is 1-10:1, preferably 2-3:1.

The reaction was carried out in an organic solvent. Said organic solvent is at least one selected from benzene, toluene, xylene, dichloromethane, chloroform, carbon tetrachloride, 1,2-dichloroethane, diethyl ether, tetrahydrofuran, methanol, ethanol, N,N-dimethyl formamide or dimethyl sulfoxide.

Preparation Method for Ezetimibe

The preparation method for Ezetimibe, the compound of formula 8 according to the present invention comprises the following steps:

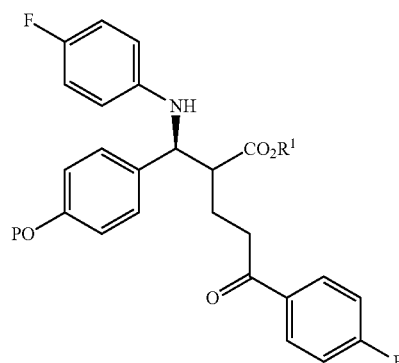

5

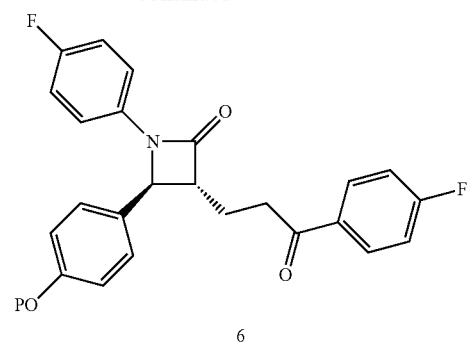

6

(i) the compound of formula 5 is subjected to a cyclization reaction under the action of a base to form the compound of formula 6;

(ii) the compound of formula 6 is subjected to asymmetric reduction reaction at the position of ketone carbonyl in an organic solvent to obtain the compound of formula 7;

(iii) a protection group is removed from the compound of formula 7 to obtain Ezetimibe, the compound of formula 8,

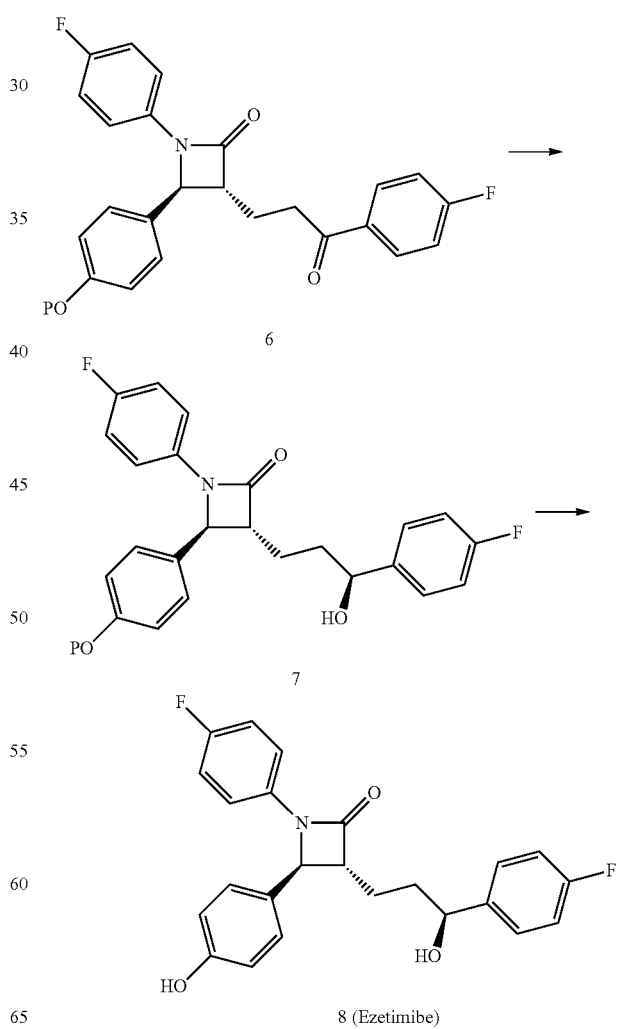

8 (Ezetimibe)

wherein P is a hydrogen, an acetyl, a propionyl, a t-butyloxycarbonyl, a benzyl, a carbobenzoxy, a trityl, a trimethylsilyl, a tert-butyldimethylsilyl or a diphenylmethylsilyl;

$R^1$ is selected from the following group: a hydrogen, a methyl, an ethyl, an isopropyl, an n-butyl, a tert-butyl, a benzyl, an allyl and an adamantly.

In another preferred embodiment, after the protection group is removed from the compound of formula 7, optically pure Ezetimibe, the compound of formula 8 is obtained by recrystallization purification.

In another preferred embodiment, the base is at least one selected from the following group: Tin(II) bis-hexamethyldisilazide ($Sn[N(TMS)_2]_2$), lithium bis(trimethylsilyl)amide (LHMDS), lithium diisopropyl amide (LDA), butyl lithium, t-butyl lithium, t-butyl magnesium chloride, t-butyl bromide magnesium, isopropyl magnesium chloride, isopropyl magnesium bromide.

In another preferred embodiment, the base is preferably lithium bis(trimethylsilyl)amide (LHMDS).

In another preferred embodiment, the mole ratio of the base to the compound of formula 5 is 1-10:1, preferably 2-3:1.

The well known methods in the art can be used in steps (i) and (ii).

In another preferred embodiment, said organic solvent is at least one selected from the following group: benzene, toluene, xylene, dichloromethane, chloroform, carbon tetrachloride, 1,2-dichloroethane, diethyl ether, tetrahydrofuran, methanol, ethanol, N,N-dimethyl formamide and dimethyl sulfoxide.

The above mentioned features of the present invention, or features mentioned in embodiments can be any combination. Any feature disclosed in the present specification can be used in combination with any other features, and each feature disclosed in the specification can be replaced with alternative feature which can serve an identical, equivalent, or similar purpose. Therefore, the features disclosed herein are only general exemplary examples of the equivalent or similar features, unless specifically indicated otherwise. Unless defined otherwise, all technical and scientific terms used herein have the same meaning as commonly understood to one of ordinary skill. In addition, any methods and materials similar or equivalent to the content with the present method can be applied in the method of the present invention.

The advantages of the invention include:

(1) the invention provides a novel intermediate of Ezetimibe;

(2) the invention provides a novel preparation method for Ezetimibe, by which the use of chiral auxiliary oxazolidone or chiral raw material can be avoided;

(3) the method according to the present invention is simple and easy to operate, and α-alkylidene-β-acylamino carbonyl compounds with high activity and selectivity can be prepared and can easily be transformed to synthesize chiral intermediates of Ezetimibe for synthesizing chiral medicament Ezetimibe.

(4) the method according to the present invention is economic and environment-friendly, reduces the cost and can be used widely.

The invention will be further illustrated with reference to the following specific examples. It should be understood that these examples are only intended to illustrate the invention, but not to limit the scope of the invention. Some nonessential improvements and adjustments made by the skilled in the art based on above contents in the present invention belong to the protection scope of the present invention. The experimental methods in the following examples without particular conditions mentioned are performed under routine conditions or as instructed by the manufacturer.

EXAMPLE 1

Preparation of Compound (R)-2a

The reaction was conducted as follows: under Argon atmosphere, $[Pd(C_3H_5)Cl]_2$ (54.8 mg, 0.15 mmol) and (S,S,S)-Lc (193 mg, 0.25 mmol) were separately added to a Schlenk tube. Anhydrous $CH_2Cl_2$ (50 mL) was added and stirred at room temperature for 10 mins. Then the substrate 1a (3.54 g, 10 mmol), $K_2CO_3$ (1.0 M aqueous solution, 30 mL, 30 mmol) and p-fluoro aniline (3.33 g, 30 mmol) were successively added and stirred at room temperature for 3 hrs. Then the reaction mixture was separated. The aqueous phase was extracted by dichloromethane (3×50 mL), and the organic phases were combined and dried on anhydrous sodium sulfate, filtered, concentrated and purified by column chromatography, so as to give (R)-2a as the product of asymmetric amination. The reaction equation was shown as below.

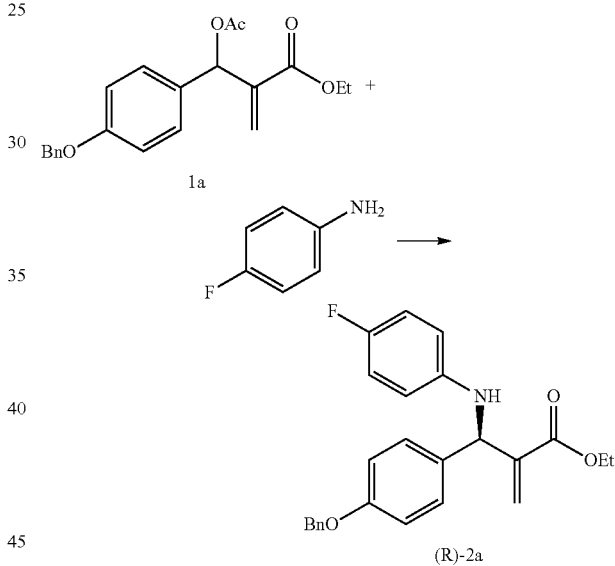

(R)-2a, white solid, 87% yield. Mp 72-73° C., $[\alpha]_D^{20}$=-111.0 (c 1.00, $CHCl_3$), 95% ee (determined by high performance liquid chromatography, chiral AD-H column, n-hexane/isopropyl alcohol=95:5, 1.0 mL/min, 254 nm; $t_R$ (minor)=21.39 min; $t_R$ (major)=24.29 min)$^1$H NMR (400 MHz, $CDCl_3$) δ=7.43-7.24 (m, 7H), 6.94-6.92 (m, 2H), 6.85 (t, J=8.8 Hz, 2H), 6.50-6.47 (m, 2H), 6.35 (t, J=0.8 Hz, 1H), 5.88 (t, J=1.2 Hz, 1H), 5.27 (s, 1H), 5.04 (s, 2H), 4.19-4.10 (m, 2H), 1.21 (t, J=7.6 Hz, 3H) ppm; $^{13}$C NMR (100 MHz, $CDCl_3$) δ=166.0, 158.2, 155.7 (d, $J_{(F,C)}$=233 Hz), 143.0 (d, $J_{(F,C)}$=1.8 Hz), 140.2 (s), 136.7 (s), 132.7 (s), 128.5 (s), 128.4 (s), 127.8 (s), 127.3 (s), 125.3 (s), 115.3 (d, $J_{(F,C)}$=21.9 Hz), 114.8 (s), 114.0 (d, $J_{(F,C)}$=7.5 Hz), 69.7, 60.6, 58.7, 13.8 ppm; $^{19}$F-NMR (376 MHz, $CDCl_3$) δ -127.5 ppm. (note: Bn is a benzyl)

EXAMPLE 2

In this example, Compound (R)-2a was prepared by catalyzing the allyl amination of substrate 1a wherein the catalyst was freshly prepared by using different phosphine ligands (S,S,S)-L and metal salt [Pd(η-C₃H₅)Cl]₂. The reaction equation was shown as below.

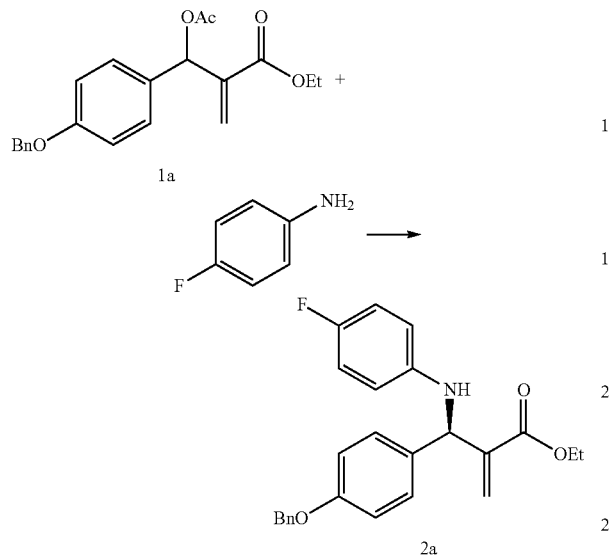

1a

2a

The reaction was conducted as follows: under Argon atmosphere, [Pd(C₃H₅)Cl]₂ (54.8 mg, 0.15 mmol) and (S,S,S)-L (0.25 mmol) were separately added to a Schlenk tube. Anhydrous CH₂Cl₂ (50 mL) was added and stirred at room temperature for 10 mins. Then the substrate 1a (3.54 g, 10 mmol), K₂CO₃ (1.0 M aqueous solution, 30 mL, 30 mmol) and p-fluoro aniline (3.33 g, 30 mmol) were successively added and stirred at room temperature for 3 hrs. Then the reaction mixture was separated. The aqueous phase was extracted by dichloromethane (3×50 mL), and the organic phases were combined and dried on anhydrous sodium sulfate, filtered, concentrated and purified by column chromatography, so as to obtain (R)-2a as the product of asymmetric amination.

TABLE 1 the results of asymmetric amination of substrate 1a

| | ligand | yield of compound 2a (%) | Ee (%) |
|---|---|---|---|
| 1 | (S,S,S)-La | 91 | (+)-93 |
| 2 | (S,S,S)-Lb | 71 | (+)-65 |
| 3 | (S,S,S)-Lc | 87 | (+)-95 |
| 4 | (S,S,S)-Ld | 85 | (+)-94 |
| 5 | (S,S,S)-Le | 87 | (+)-92 |
| 6 | (S,S,S)-Lf | 91 | (+)-90 |
| 7 | (S,S,S)-Lg | 86 | (+)-92 |
| 8 | (S,S,S)-Lh | 90 | (+)-91 |
| 9 | (S,S,S)-Li | 79 | (+)-88 |

EXAMPLE 3

Preparation of Compound (R)-2a

The reaction was conducted as follows: under Argon atmosphere, [Pd(C₃H₅)Cl]₂ (54.8 mg, 0.15 mmol) and (S,S,S)-Lc (193 mg, 0.25 mmol) were separately added to a Schlenk tube. Anhydrous CH₂Cl₂ (50 mL) was added and stirred at room temperature for 10 mins. Then the substrate 1b (4.12 g, 10 mmol), K₂CO₃ (1.0 M aqueous solution, 30 mL, 30 mmol) and p-fluoro aniline (3.33 g, 30 mmol) were successively added and stirred at room temperature for 3 hrs. Then the reaction mixture was separated. The aqueous phase was extracted by dichloromethane (3×50 mL), and the organic phases were combined and dried on anhydrous sodium sulfate, filtered, concentrated and purified by column chromatography, so as to obtain (R)-2a as the product of asymmetric amination. The reaction equation was shown as below.

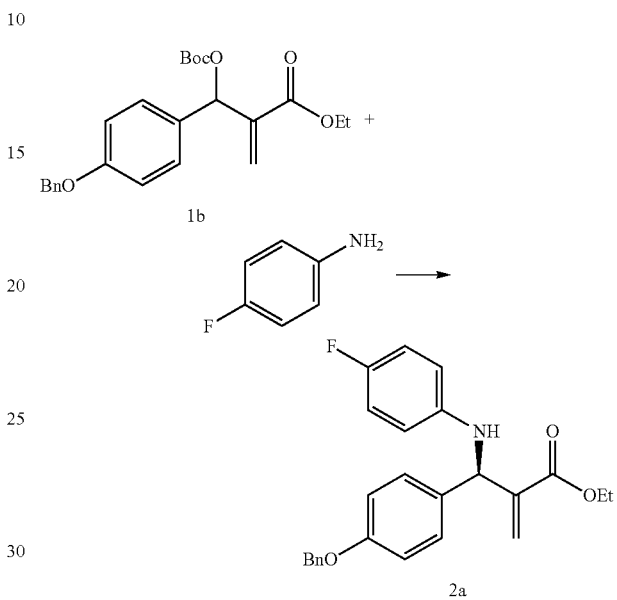

1b

2a (R)-2a, 85% yield, 93% ee.

EXAMPLE 4

Preparation of Compound (R)-2b

The reaction was conducted as follows: under Argon atmosphere, [Pd(C₃H₅)Cl]₂ (54.8 mg, 0.15 mmol) and (S,S,S)-La (165 mg, 0.25 mmol) were separately added to a Schlenk tube. Anhydrous CH₂Cl₂ (50 mL) was added and stirred at room temperature for 10 mins. Then the substrate 1b (3.78 g, 10 mmol), K₂CO₃ (1.0 M aqueous solution, 30 mL, 30 mmol) and p-fluoro aniline (3.33 g, 30 mmol) were successively added and stirred at room temperature for 3 hrs. Then the reaction mixture was separated. The aqueous phase was extracted by dichloromethane (3×50 mL), and the organic phases were combined and dried on anhydrous sodium sulfate, filtered, concentrated and purified by column chromatography, so as to obtain (R)-2b as the product of asymmetric amination. The reaction equation was shown as below.

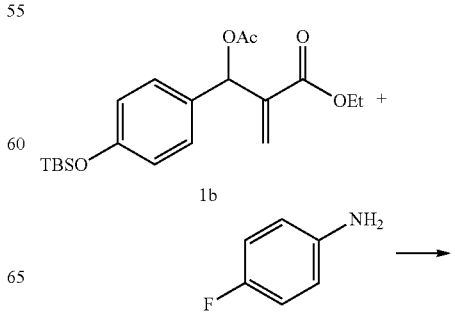

1b

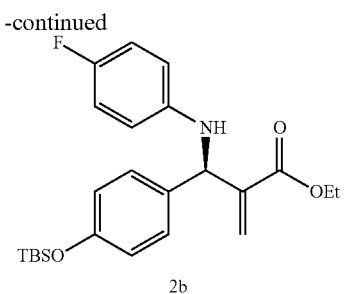

2b (R)-2b, colorless liquid, 86% yield, $[\alpha]_D^{20}=-89.1$ (c 1.00, CHCl$_3$), 95% ee (determined by high performance liquid chromatography, chiral AD-H column, n-hexane/isopropyl alcohol=95:5, 1.0 mL/min, 254 nm; $t_R$ (minor)=4.15 min; $t_R$ (major)=4.60 min)$^1$H NMR (300 MHz, CDCl$_3$) δ=7.20 (d, J=8.4 Hz, 2H), 6.89-6.78 (m, 4H), 6.51-6.47 (m, 2H), 6.34 (s, 1H), 5.88 (s, 1H), 5.26 (s, 1H), 4.19-4.08 (m, 2H), 4.00 (s, br, 1H), 1.20 (t, J=7.2 Hz, 3H), 0.97 (s, 9H), 0.18 (s, 6H) ppm; $^{13}$C NMR (100 MHz, CDCl$_3$) δ=166.1, 155.8 (d, $J_{(F,C)}$=234.3 Hz), 155.1 (s), 143.0 (d, $J_{(F,C)}$=1.9 Hz), 140.4 (s), 133.1 (s), 128.5 (s), 125.2 (s), 120.0 (s), 115.4 (d, $J_{(F,C)}$=22.3 Hz), 114.1 (d, $J_{(F,C)}$=7.4 Hz), 60.6, 58.9, 25.5, 18.0, 13.9, -4.5 ppm; $^{19}$F-NMR (376 MHz, CDCl$_3$) δ -127.5 ppm.

EXAMPLE 5

Preparation of Compound 4a (R)-2a (3.44 g, 8.48 mmol) and nucleophilic reagent 3a (2.82 g, 12.7 mmol) were added to an eggplant-shaped flask, and then tetrahydrofuran (100 mL) and DBU (4.25 g, 16.96 mmol) were added. The reaction mixture was stirred at room temperature for 12 hrs and thin-layer chromatography TLC confirmed that the raw materials disappeared. The reaction liquid was concentrated and purified by column chromatography to obtain compound 4a, 82% yield. (note: Allyl is allyl group)

ESI-MS m/z: 628.4 [M+H$^+$]; HRMS (ESI) m/z: calcd. for C$_{37}$H$_{36}$NO$_6$F$_2^{+1}$: 628.2505, Found: 628.2504 [M+H$^+$].

The reaction system can be directly used in next step without post-processing. The reaction equation was shown as below.

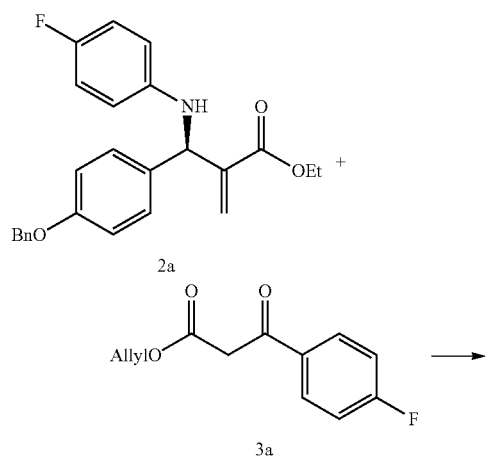

2a

3a

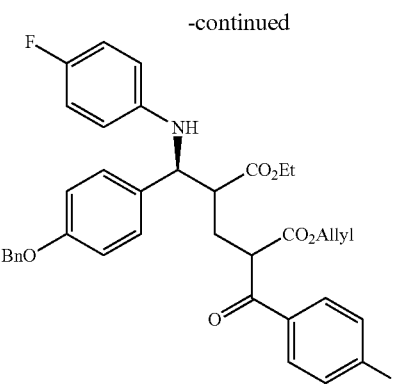

4a

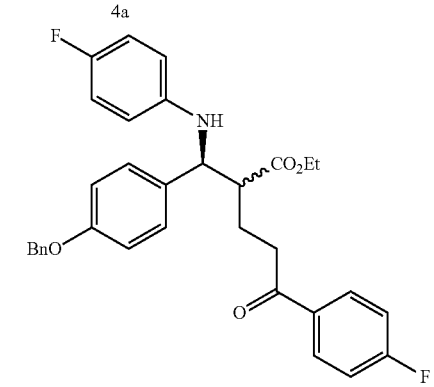

5a

EXAMPLE 6

Preparation of Compound 5a

Morpholine (4.43 g, 50.88 mmol) and Pd(PPh$_3$)$_4$ (98 mg, 0.0848 mmol) were added to the reaction system obtained in example 5 and stirred at room temperature for 6 hrs. The reaction mixture was concentrated and purified by column chromatography.

The total yield from compound 2a to 5a was 71%. Compound 5a was composed of a pair of diastereomers with the ratio of 2-3:1. The diastereomers can be directly used in next step without being separated.

ESI-MS m/z: 544.2 [M+H$^+$]; HRMS (ESI) m/z: calcd. for C$_{33}$H$_{31}$NO$_4$F$_2$Na$^{+1}$: 566.2113, Found: 566.2113 [M+Na$^+$].

EXAMPLE 7

Preparation of Compound 6a

Compound 5a (3.5 g, 6.4 mmol) and anhydrous tetrahydrofuran (50 mL) were added to an eggplant-shaped flask and cooled to below −20° C. Lithium bis(trimethylsilyl) amide (LiHMDS) (1.0 M THF, 14 ml, 14 mmol) was slowly added dropwise. The reaction system was stirred at the above temperature for 40 mins and 5 mL of water was added to quench the reaction. The reaction mixture was extracted by dichloromethane (3×100 mL), and the organic phase was dried on anhydrous solium sulfate, filtered, concentrated and purified by column chromatography. Compound 6a was obtained.

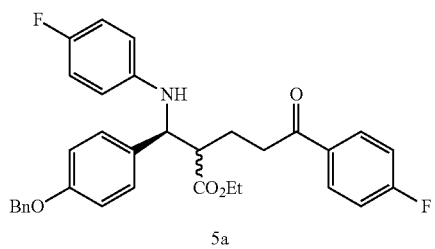

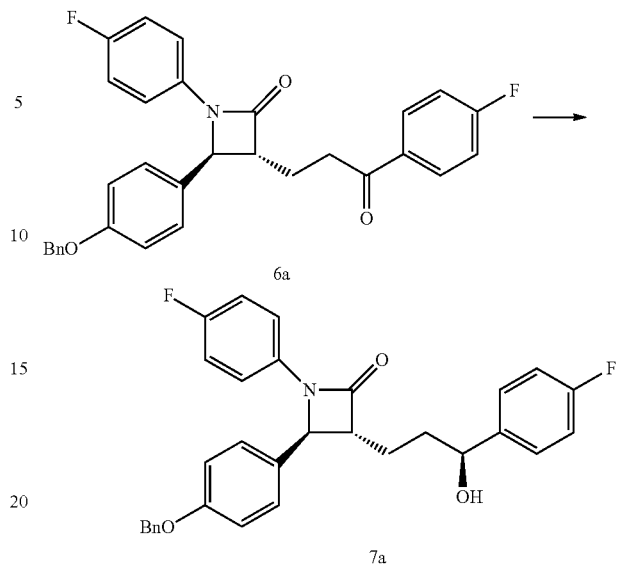

6a, 77% yield. $[\alpha]_D^{20}$=+1.9 (c 1.00, MeOH), 95% ee (determined by high performance liquid chromatography, chiral OD-H column, n-hexane/isopropyl alcohol=70:30, 10 mL/min, 254 nm; $t_R$ (major)=19.60 min; $t_R$ (minor)=25.83 min) $^1$H NMR (400 MHz, CDCl$_3$) δ=7.98-7.94 (m, 2H), 7.41-7.30 (m, 5H), 7.25-7.23 (m, 4H), 7.09 (t, J=8.8 Hz, 2H), 6.96-6.88 (m, 4H), 5.02 (s, 1H), 4.67 (d, J=2.4 Hz, 1H), 3.31-3.23 (m, 1H), 3.17-3.08 (m, 2H), 2.42-2.20 (m, 2H) ppm; $^{13}$C NMR (100 MHz, CDCl$_3$) δ=197.2, 167.1, 165.6 (d, $J_{(F,C)}$=253.9 Hz), 158.9, 158.8 (d, $J_{(F,C)}$=242.2 Hz), 136.5, 133.7 (d, $J_{(F,C)}$=2.7 Hz), 132.9 (d, $J_{(F,C)}$=2.8 Hz), 130.5 (d, $J_{(F,C)}$=9.4 Hz), 129.3, 128.5, 127.9, 127.3, 127.1, 118.2 (d, $J_{(F,C)}$=7.9 Hz), 115.7 (d, $J_{(F,C)}$=8.4 Hz), 115.5 (d, $J_{(F,C)}$=8.3 Hz), 115.3, 69.9, 60.9, 59.6, 35.4, 23.0 ppm; $^{19}$F NMR (376 MHz, CDCl$_3$) δ −104.8, −117.9 ppm.

The specific rotatory direction and NMR data of compound 6a were the same as those reported in literatures.

Literatures: (a) Wu, G.; Wong, Y.; Chen, X.; Ding, Z. *J. Org. Chem.* 1999, 64, 3714. (b) Sasikala, C. H. V. A.; Padi, P. R.; Sunkara, V.; Ramayya, P.; Dubey, P. K.; Uppala, V. B. R.; Praveen, C. *Org. Process Res. Dev.* 2009, 13, 907. (c) Soya, M.; Mravljak, J.; Kovač, A.; Pečar, S.; Časar, Z.; Gobec, S.; *Synthesis,* 2010, 20, 3433.

EXAMPLE 8

Preparation of Compound 7a

Dichloromethane (40 mL) and tetrahydrofuran (5 mL) were separately added to an eggplant-shaped flask and cooled to 0° C. Then borane-dimethyl sulfide complex (0.46 mL, 7.23 mmol) and (R)-(+)-2-methyl-CBS-oxazaborolidine (133 mg, 0.482 mmol) were added. Compound 6a (2.4 g, 4.82 mmol) was dissolved in dichloromethane (20 mL) and added. The reaction mixture was stirred at the same temperature for 5 hrs. After the reaction was completed, methanol (10 mL) was used to quench the reaction. The mixture was concentrated and 1 mol/l diluted hydrochloric acid was added to acidize the mixture. The resulting mixture was extracted by dichloromethane (x), and the organic phase was washed with saturated sodium chloride, concentrated and recrystallized in ethyl acetate/n-hexane to obtain compound 7a in 90% yield and >99% ee. The reaction equation was shown as below.

7a, $^1$H-NMR (300 MHz, CDCl$_3$) δ=7.47-7.21 (m, 11H), 7.07-6.92 (m, 6H), 5.05 (s, 2H), 4.75-4.72 (m, 1H), 4.58 (m, 1H), 3.17-3.09 (m, 1H), 2.04-1.85 (m, 4H) ppm.

EXAMPLE 9

Preparation of Compound 8

7a (2.14 g, 4.3 mmol), methanol (30 mL) and Pd/C (50 mg) were added to a hydrogenation flask and transferred to a high pressure reactor. Hydrogen displacement was performed for three times, and then the reactor was charged with 5 atm of hydrogen. The reaction mixture was stirred at room temperature for 6 hrs and hydrogen was discharged. Then the reaction mixture was filtered by celite, washed with a small amount methanol (10 mL) and concentrated. The residue was recrystallized in a mixed solvent of methyl tertiary butyl ether and n-hexane to obtain compound 8 in 78% yield.

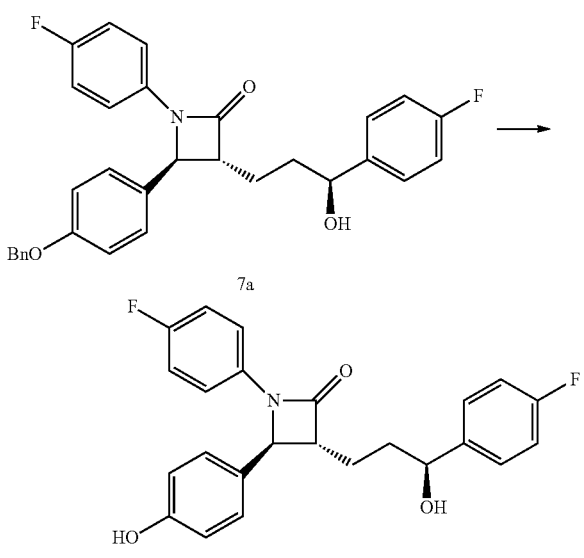

8, $^1$H-NMR (300 MHz, DMSO-d$_6$) δ=9.50 (s, 1H), 7.41-7.07 (m, 10H), 6.79 (d, J=8.6 Hz, 2H), 5.27-5.25 (m, 1H), 4.78-4.71 (m, 1H), 4.47-4.44 (m, 1H), 3.07-3.08 (m, 1H), 1.85-1.75 (m, 4H) ppm.

EXAMPLE 10

Preparation of Compound La (P=Bn, Benzyl)

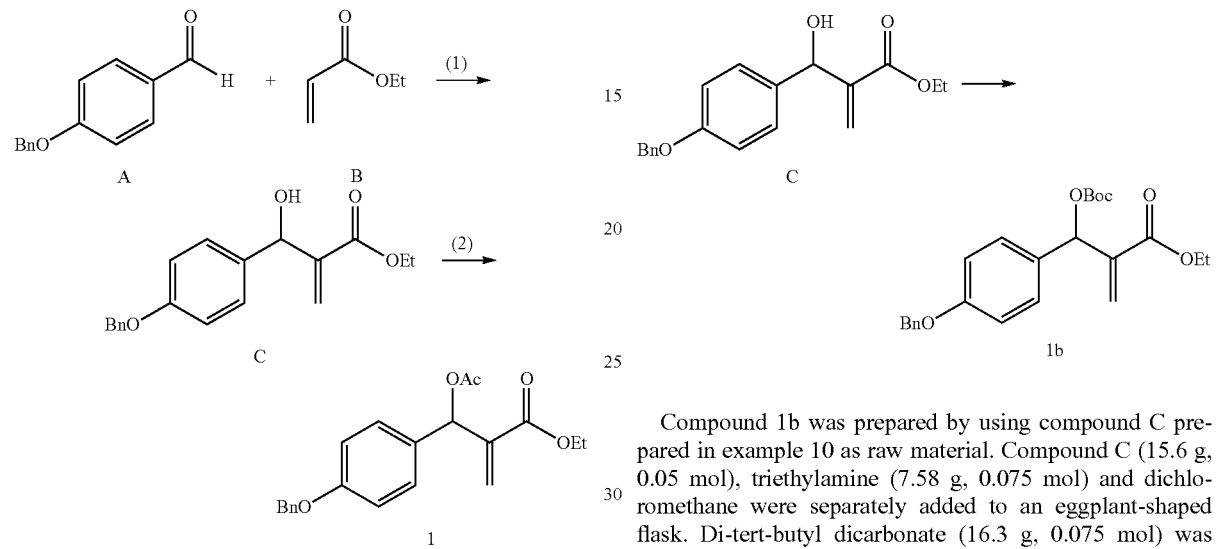

Step 1: 4-benzyloxybenzaldehyde (21.2 g, 0.1 mol), ethyl acrylate (10.0 g, 0.1 mol) and 1,4-diazabicyclo[2.2.2]octane (DABCO, 11.2 g, 0.1 mol) were separately added to an eggplant-shaped flask and heated to 45° C. in an oil bath. After stirred for 10 days, the reaction mixture was cooled to room temperature and 100 mL of water was added. The resulting mixture was extracted by ethyl acetate, and the organic phase was dried on anhydrous sodium sulfate, filtered and concentrated. The residue was purified by column chromatography to obtain compound C in 55% yield.

White solid, Mp 66-67° C. $^1$H NMR (300 MHz, CDCl$_3$) δ=7.41-7.24 (m, 7H), 6.92 (d, J=8.7 Hz, 2H), 6.30 (s, 1H), 5.83 (s, 1H), 5.48 (s, 1H), 5.01 (s, 2H), 4.12 (q, J=6.9 Hz, 2H), 3.15 (s, br, 1H), 1.21 (t, J=6.9 Hz, 3H) ppm; $^{13}$C NMR (75 MHz, CDCl$_3$) δ=166.2, 158.2, 142.2, 136.7, 133.7, 128.4, 127.9, 127.8, 127.3, 125.1, 114.5, 72.5, 69.8, 60.7, 13.9 ppm.

Step 2: Compound C (15.6 g, 0.05 mol) obtained in step 1, pyridine (5.9 g, 0.075 mol) and dichloromethane were separately added to an eggplant-shaped flask and acetylchloride (5.88 g, 0.075 mol) was slowly added. Upon addition, the reaction mixture was stirred at room temperature for 1 hr. Saturated sodium bicarbonate solution was added to quench the reaction and the reaction mixture was separated. The aqueous phase was extracted with dichloromethane, and the organic phases were combined, dried on anhydrous sodium sulfate and filtered. The filtrate was concentrated. The residue was purified by column chromatography to obtain compound 1a in 92% yield.

White solid, Mp 60-61° C., $^1$H NMR (400 MHz, CDCl$_3$) δ=7.40-7.29 (m, 7H), 6.92 (d, J=8.8 Hz, 2H), 6.64 (s, 1H), 6.37 (s, 1H), 5.83 (s, 1H), 5.01 (s, 2H), 4.16-4.08 (m, 2H), 2.06 (s, 3H), 1.19 (t, J=7.2 Hz, 3H) ppm; $^{13}$C NMR (100 MHz, CDCl$_3$) δ=169.2, 164.8, 158.6, 139.7, 136.6, 129.9, 129.0, 128.4, 127.8, 127.3, 124.7, 114.5, 72.7, 69.7, 60.7, 20.9, 13.8 ppm.

EXAMPLE 11

Preparation of Compound 1b

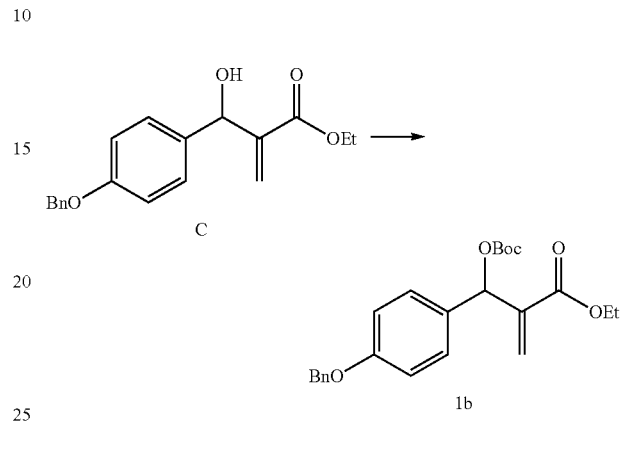

Compound 1b was prepared by using compound C prepared in example 10 as raw material. Compound C (15.6 g, 0.05 mol), triethylamine (7.58 g, 0.075 mol) and dichloromethane were separately added to an eggplant-shaped flask. Di-tert-butyl dicarbonate (16.3 g, 0.075 mol) was slowly added and stirred at room temperature for 2 hrs. Saturated sodium bicarbonate solution was added to quench the reaction and the reaction mixture was separated. The aqueous phase was extracted with dichloromethane, and the organic phases were combined and dried on anhydrous sodium sulfate and filtered. The filtrate was concentrated. The residue was purified by column chromatography to obtain compound 1b in 92% yield. $^1$H NMR (400 MHz, CDCl$_3$) δ=7.42-7.25 (m, 7H), 6.95 (d, J=9.2 Hz, 2H), 6.68 (s, 1H), 6.39 (s, 1H), 5.79 (s, 1H), 5.12 (s, 2H), 4.11-4.01 (m, 2H), 1.63 (s, 9H), 1.19 (t, J=7.2 Hz, 3H), 0.89 (s, 6H) ppm.

EXAMPLE 12

Preparation of Compound 1c (P=TBS, t-Butyldimethylsilyl)

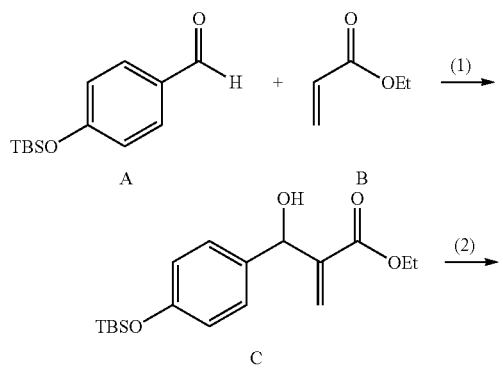

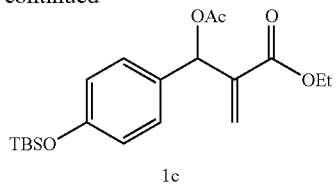

1c

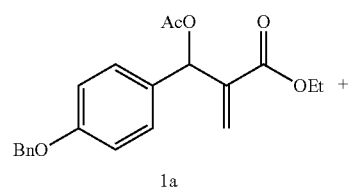

1a

Step 1: 4-(t-butyldimethylsiloxy)benzaldehyde (23.6 g, 0.1 mol), ethyl acrylate (10.0 g, 0.1 mol) and 1,4-diazabicyclo[2.2.2]octane (DABCO, 11.2 g, 0.1 mol) were separately added to an eggplant-shaped flask and stirred at room temperature for 10 days. 100 mL of water was added and the resulting mixture was extracted by ethyl acetate. The organic phase was dried on anhydrous sodium sulfate and filtered and concentrated. The residue was purified by column chromatography to obtain compound C in 55% yield.

Oily liquid, $^1$H NMR (400 MHz, CDCl$_3$) δ=7.15 (d, J=8.7 Hz, 2H), 6.74 (d, J=8.7 Hz, 2H), 6.24 (s, 1H), 5.77 (s, 1H), 5.43 (s, 1H), 4.11-4.01 (m, 2H), 3.35 (s, br, 1H), 1.15 (t, J=7.2 Hz, 3H), 0.93 (s, 9H), 0.14 (s, 6H) ppm; $^{13}$C NMR (75 MHz, CDCl$_3$) δ=166.1, 155.0, 142.4, 134.1, 127.8, 124.9, 119.6, 72.3, 60.5, 25.4, 17.9, 13.8, −4.6 ppm.

Step 2: Compound C obtained in step 1 (16.8 g, 0.05 mol), pyridine (5.9 g, 0.075 mol) and dichloromethane were separately added to an eggplant-shaped flask and acetylchloride (5.88 g, 0.075 mol) was slowly added. Upon addition, the reaction mixture was stirred at room temperature for 1 hr. Saturated sodium bicarbonate solution was added to quench the reaction and the reaction mixture was separated. The aqueous phase was extracted with dichloromethane, and the organic phases were combined and dried on anhydrous sodium sulfate and filtered. The filtrate was concentrated. The residue was purified by column chromatography to obtain compound 1 in 90% yield.

Colorless liquid, $^1$H NMR (300 MHz, CDCl$_3$) δ=7.16 (d, J=8.1 Hz, 2H), 6.72 (d, J=8.4 Hz, 2H), 6.56 (s, 1H), 6.29 (s, 1H), 5.73 (s, 1H), 4.12-4.01 (m, 2H), 2.00 (s, 3H), 1.11 (t, J=7.2 Hz, 3H), 0.90 (s, 9H), 0.11 (s, 6H) ppm; $^{13}$C NMR (75 MHz, CDCl$_3$) δ=169.2, 164.8, 155.5, 139.9, 130.3, 128.9, 124.7, 119.7, 72.6, 60.6, 25.4, 20.9, 18.0, 13.8, −4.6 ppm.

EXAMPLE 13

Preparation of Racemic Compound 2a

The reaction was conducted as follows: under Argon atmosphere, [Pd(C$_3$H$_5$)Cl]$_2$ (54.8 mg, 0.15 mmol) and racemic biphosphine ligand La (165 mg, 0.25 mmol) were separately added to a Schlenk tube. Anhydrous CH$_2$Cl$_2$ (50 mL) was added and stirred at room temperature for 10 mins. Then the substrate 1a (3.54 g, 10 mmol), K$_2$CO$_3$ (1.0 M aqueous solution, 30 mL, 30 mmol) and p-fluoro aniline (3.33 g, 30 mmol) were successively added. The reaction mixture was stirred at room temperature for 1 hr and separated. The aqueous phase was extracted with dichloromethane (3×50 mL), and the organic phases were combined and dried on anhydrous sodium sulfate, filtered, concentrated and purified by column chromatography to obtain racemic compound 2a as amination product in 89% yield. The reaction equation was shown as below.

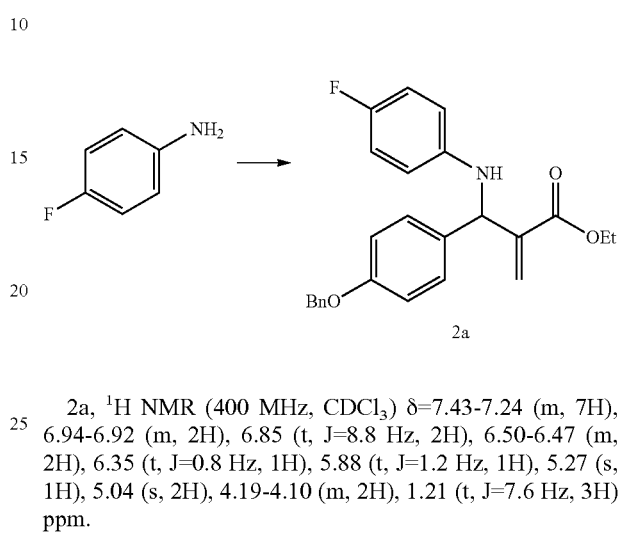

2a

2a, $^1$H NMR (400 MHz, CDCl$_3$) δ=7.43-7.24 (m, 7H), 6.94-6.92 (m, 2H), 6.85 (t, J=8.8 Hz, 2H), 6.50-6.47 (m, 2H), 6.35 (t, J=0.8 Hz, 1H), 5.88 (t, J=1.2 Hz, 1H), 5.27 (s, 1H), 5.04 (s, 2H), 4.19-4.10 (m, 2H), 1.21 (t, J=7.6 Hz, 3H) ppm.

EXAMPLE 14

Preparation of Racemic Compound 2b

The reaction was conducted as follows: under Argon atmosphere, [Pd(C$_3$H$_5$)Cl]$_2$ (54.8 mg, 0.15 mmol) and racemic bisphosphine ligand La (165 mg, 0.25 mmol) were separately added to a Schlenk tube. Anhydrous CH$_2$Cl$_2$ (50 mL) was added and stirred at room temperature for 10 mins. Then the substrate 1c (3.78 g, 10 mmol), K$_2$CO$_3$ (1.0 M aqueous solution, 30 mL, 30 mmol) and p-fluoro aniline (3.33 g, 30 mmol) were successively added. The reaction mixture was stirred at room temperature for 3 hrs and separated. The aqueous phase was extracted with dichloromethane (3×50 mL), and the organic phases were combined and dried on anhydrous sodium sulfate, filtered, concentrated and purified by column chromatography to obtain racemic compound 2b as amination product in 83% yield.

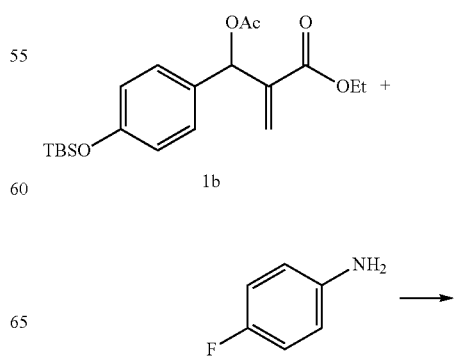

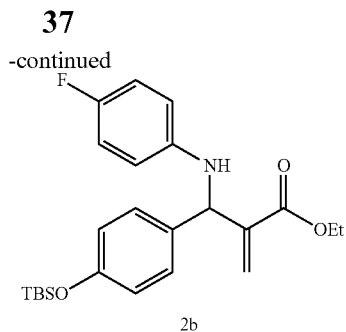

2b, $^1$H NMR (300 MHz, CDCl$_3$) δ=7.20 (d, J=8.4 Hz, 2H), 6.89-6.78 (m, 4H), 6.51-6.47 (m, 2H), 6.34 (s, 1H), 5.88 (s, 1H), 5.26 (s, 1H), 4.19-4.08 (m, 2H), 4.00 (s, br, 1H), 1.20 (t, J=7.2 Hz, 3H), 0.97 (s, 9H), 0.18 (s, 6H) ppm.

EXAMPLE 15

Preparation of Racemic Compound 4a

Racemic 2a (3.44 g, 8.48 mmol) and nucleophile 3a (2.82 g, 12.7 mmol) were separately added to an eggplant-shaped flask. Then tetrahydrofuran (100 mL) and DBU (4.25 g, 16.96 mmol) were added. The reaction mixture was stirred at room temperature for 12 hrs and TLC confirmed that the raw materials disappeared. The reaction liquid was concentrated and purified by column chromatography to obtain compound 4a in 84% yield. The reaction system can be directly used in next step without being post-processed. The reaction equation was shown as below.

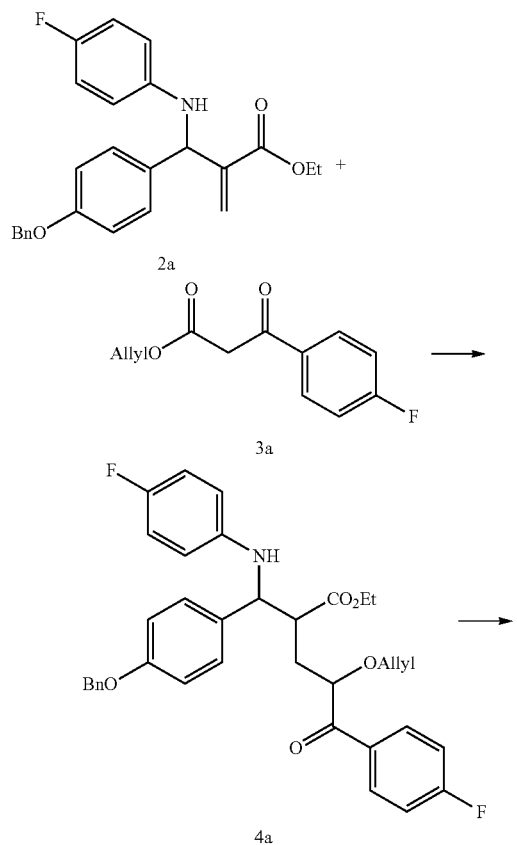

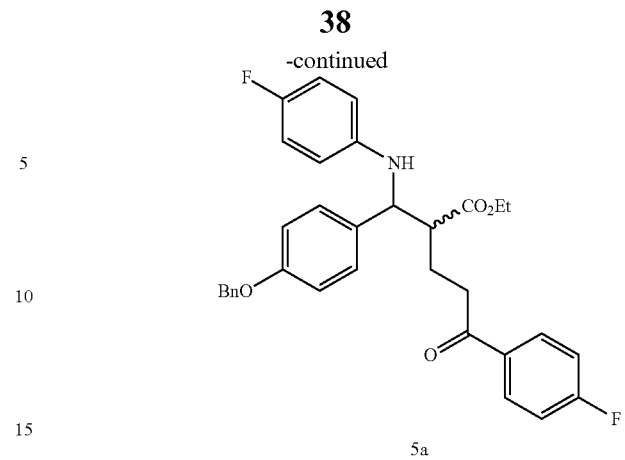

ESI-MS m/z: 628.5 [M+H$^+$]; HRMS (ESI) m/z: calcd. for C$_{37}$H$_{36}$NO$_6$F$_2$$^{+1}$: 628.2505, Found: 628.2506 [M+H$^+$].

EXAMPLE 16

Preparation of Racemic Compound 5a

Morpholine (4.43 g, 50.88 mmol) and Pd(PPh$_3$)$_4$ (98 mg, 0.0848 mmol) were added to the reaction system obtained in example 15 and stirred at room temperature for 6 hrs. The reaction mixture was concentrated and purified by column chromatography.

The total yield from compound 2a to 5a was 68%.

ESI-MS m/z: 544.2 [M+H$^+$]; HRMS (ESI) m/z: calcd. for C$_{33}$H$_{31}$NO$_4$F$_2$Na$^{+1}$: 566.2113, Found: 566.2113 [M+Na$^+$].

EXAMPLE 17

Preparation of Compound (S)-2a

The reaction was conducted as follows: under Argon atmosphere, [Pd(C$_3$H$_5$)Cl]$_2$ (54.8 mg, 0.15 mmol) and (R,R,R)-La (165 mg, 0.25 mmol) were separately added to a Schlenk tube. Anhydrous CH$_2$Cl$_2$ (50 mL) was added and stirred at room temperature for 10 mins. Then the substrate 1a (3.54 g, 10 mmol), K$_2$CO$_3$ (1.0 M aqueous solution, 30 mL, 30 mmol) and p-fluoro aniline (3.33 g, 30 mmol) were successively added. The reaction mixture was stirred at room temperature for 3 hrs and separated. The aqueous phase was extracted with dichloromethane (3×50 mL), and the organic phases were combined and dried on anhydrous sodium sulfate, filtered, concentrated and purified by column chromatography to obtain (S)-2a as amination product in 89% yield and 94% ee. The reaction equation was shown as below.

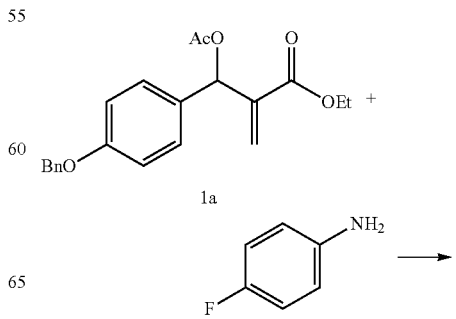

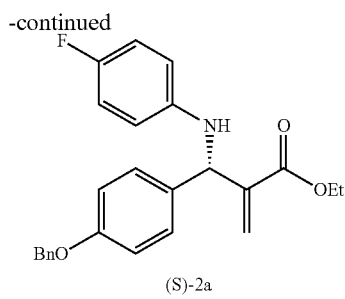

(S)-2a (S)-2a, white solid, 81% yield. $[\alpha]_D^{20}=+113.0$ (c 1.00, CHCl$_3$), 95% ee (determined by high performance liquid chromatography, chiral AD-H column, n-hexane/isopropyl alcohol=95:5, 1.0 mL/min, 254 nm; $t_R$ (major)=21.45 min; $t_R$ (minor)=24.27 min)$^1$H NMR (400 MHz, CDCl$_3$) δ=7.43-7.24 (m, 7H), 6.94-6.92 (m, 2H), 6.85 (t, J=8.8 Hz, 2H), 6.50-6.47 (m, 2H), 6.35 (t, J=0.8 Hz, 1H), 5.88 (t, J=1.2 Hz, 1H), 5.27 (s, 1H), 5.04 (s, 2H), 4.19-4.10 (m, 2H), 1.21 (t, J=7.6 Hz, 3H) ppm.

EXAMPLE 18

Preparation of Compound (S)-2b

The reaction was conducted as follows: under Argon atmosphere, [Pd(C$_3$H$_5$)Cl]$_2$ (54.8 mg, 0.15 mmol) and (R,R,R)-La (165 mg, 0.25 mmol) were separately added to a Schlenk tube. Anhydrous CH$_2$Cl$_2$ (50 mL) was added and stirred at room temperature for 10 mins. Then the substrate 1c (3.78 g, 10 mmol), K$_2$CO$_3$ (1.0 M aqueous solution, 30 mL, 30 mmol) and p-fluoro aniline (3.33 g, 30 mmol) were successively added. The reaction mixture was stirred at room temperature for 3 hrs and separated. The aqueous phase was extracted with dichloromethane (3×50 mL), and the organic phases were combined and dried on anhydrous sodium sulfate, filtered, concentrated and purified by column chromatography to obtain (S)-2b as amination product in 87% yield.

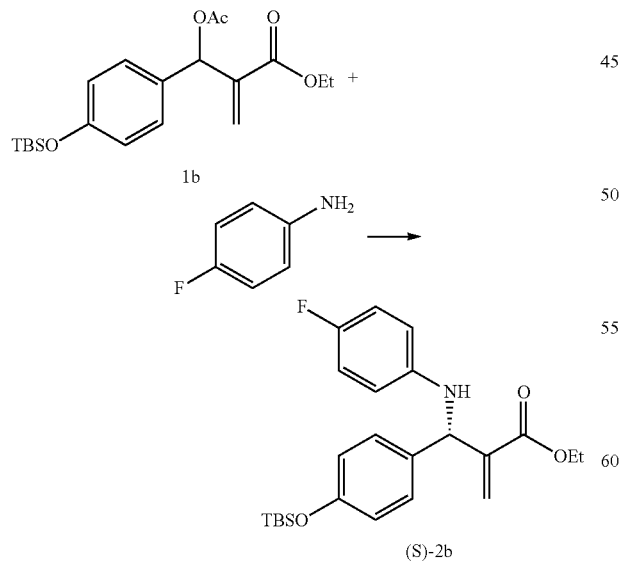

(S)-2b, colorless liquid, 86% yield, $[\alpha]_D^{20}=+89.9$ (c 1.00, CHCl$_3$), 95% ee (determined by high performance liquid chromatography, chiral AD-H column, n-hexane/isopropyl alcohol=95:5, 1.0 mL/min, 254 nm; $t_R$ (major)=4.19 min; $t_R$ (minor)=4.63 min)$^1$H NMR (300 MHz, CDCl$_3$) δ=7.20 (d, J=8.4 Hz, 2H), 6.89-6.78 (m, 4H), 6.51-6.47 (m, 2H), 6.34 (s, 1H), 5.88 (s, 1H), 5.26 (s, 1H), 4.19-4.08 (m, 2H), 4.00 (s, br, 1H), 1.20 (t, J=7.2 Hz, 3H), 0.97 (s, 9H), 0.18 (s, 6H) ppm.

EXAMPLE 19

Preparation of Compound 4a (S)-2a (3.44 g, 8.48 mmol) and nucleophile 3a (2.82 g, 12.7 mmol) were added to an eggplant-shaped flask. Then tetrahydrofuran (100 mL) and DBU (4.25 g, 16.96 mmol) were added. The reaction mixture was stirred at room temperature for 12 hrs and TLC confirmed that the raw materials disappeared. The reaction system was directly used in next step without being post-processed. The reaction equation was shown as below.

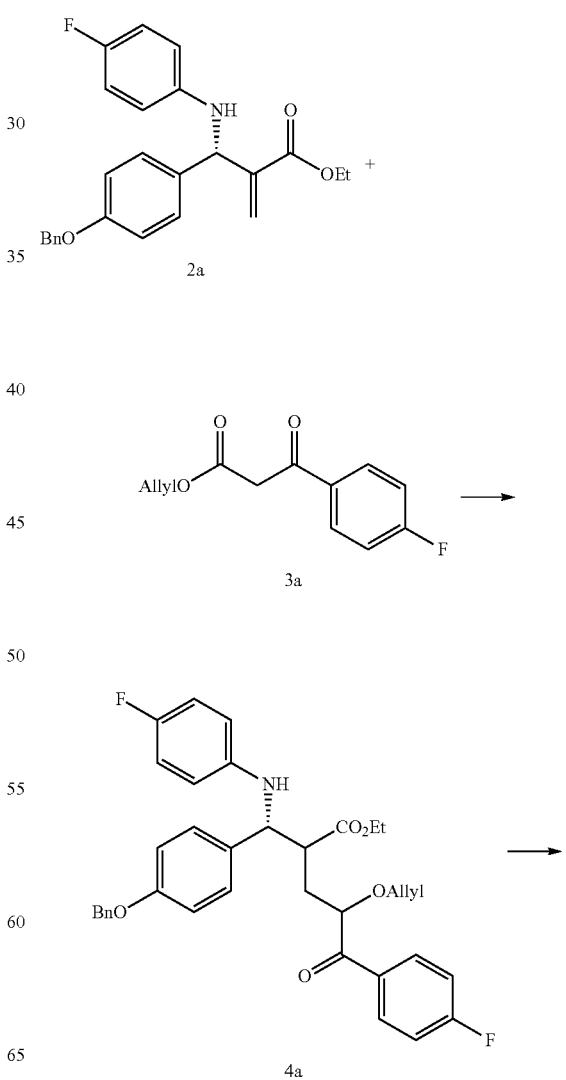

-continued

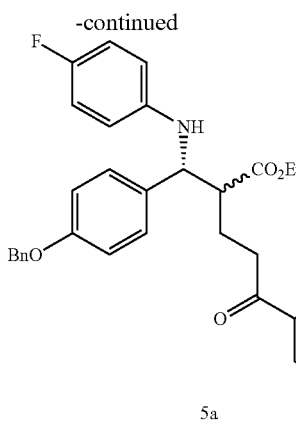

5a

ESI-MS m/z: 628.2 [M+H$^+$]; HRMS (ESI) m/z: calcd. for C$_{37}$H$_{36}$NO$_6$F$_2$$^{+1}$: 628.2505, Found: 628.2508 [M+H$^+$].

EXAMPLE 20

Preparation of Compound 5a

Morpholine (4.43 g, 50.88 mmol) and Pd(PPh$_3$)$_4$ (98 mg, 0.0848 mmol) were added to the reaction system obtained in example 19 and stirred at room temperature for 6 hrs. The reaction mixture was concentrated and purified by column chromatography.
The total yield from compound 2a to 5a was 74%.
ESI-MS m/z: 544.4 [M+H$^+$]; HRMS (ESI) m/z: calcd. for C$_{33}$H$_{31}$NO$_4$F$_2$Na$^{+1}$: 566.2113, Found: 566.2115 [M+Na$^+$].

EXAMPLE 21

Preparation of Compound 9

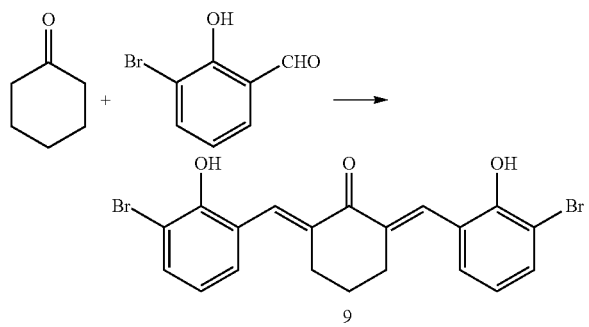

3-bromosalicylaldehyde (10.25 g, 51.0 mmol), cyclohexanone (2.5 mL, 25.0 mmol), ethanol (20.0 mL) and aqueous sodium hydroxide solution (20 wt %, 15 mL) were added to a 50 mL one-necked flask and stirred at room temperature for 24 hrs. 100 mL of distilled water was added to the reaction system and pH was adjusted to 5 by 6 mol/L aqueous hydrochloric acid solution. The reaction mixture was filtered, and the solid was washed with distilled water and recrystallized in acetone-petroleum ether to obtain 4.6 g of formula 9 compound as yellow solid in 60% yield.
Compound 9, mp 174-175° C.; $^1$H NMR (400 MHz, DMSO-d$_6$) δ 9.62 (s, br, 2H), 7.75 (s, 2H), 7.54 (d, J=8.0 Hz, 2H), 7.29 (d, J=7.6 Hz, 2H), 6.86 (t, J=8.0 Hz, 2H), 2.76 (t, J=5.6 Hz, 4H), 1.68-1.62 (m, 2H) ppm; $^{13}$C NMR (100 MHz, DMSO-d$_6$) δ 188.9, 152.5, 137.1, 133.3, 131.5, 129.5, 125.8, 120.9, 111.8, 28.0, 22.8 ppm.

EXAMPLE 22

Preparation of Compound (R,R,R)-10

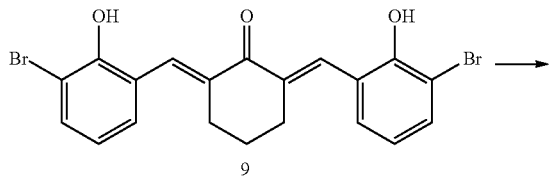

9

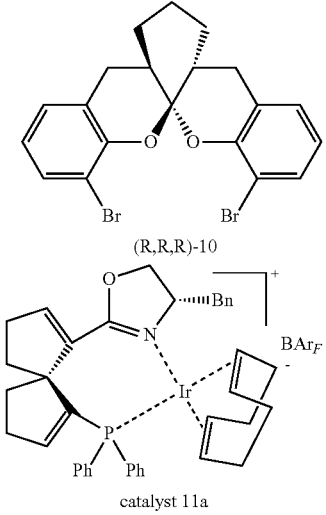

(R,R,R)-10 catalyst 11a

Chiral aromatic spiroketal compound (R,R,R)-10 was prepared by using compound 9 prepared in example 21 as hydrogenation substrate and compound 11a as catalyst. The reaction was conducted as follows: 9 (46.4 mg, 0.1 mmol), and catalyst 11a (1.6 mg, 0.001 mmol) and 2 mL of anhydrous dichloromethane were added to a hydrogenation flask. The hydrogenation flask was placed in glovebox and transferred to a high pressure reactor. Hydrogen displacement was performed for three times, and then the reactor was charged with 50 atm of hydrogen. The reaction was carried out at room temperature for 24 hrs. After hydrogen was discharged, the reactor was opened and the solvent was removed under reduced pressure. The residue was separated by column chromatography to obtain (R,R,R)-5a with >99% ee in 93% yield.
(R,R,R)-10, white solid, mp 97-98° C.; [α]$_D$$^{20}$=−85.2 (c 0.80, CHCl$_3$), >99% ee (determined by high performance liquid chromatography, chiral AD-H column, n-hexane/isobutyl alcohol=99:1, 0.5 mL/min, 230 nm; t$_R$ (major)=11.74 min; t$_R$ (minor)=13.10 min)$^1$H NMR (300 MHz, CDCl$_3$) δ 7.36 (dd, J=8.1, 0.9 Hz, 2H), 7.03 (dd, J=7.5, 0.6 Hz, 2H), 6.77 (t, J=7.5 Hz, 2H), 3.05 (dd, J=16.8, 6.3 Hz, 2H), 2.70 (dd, J=16.8 Hz, 7.2 Hz, 2H), 2.40-2.36 (m, 2H), 1.85-1.80 (m, 2H), 1.62-1.50 (m, 4H) ppm; $^{13}$C NMR (75 MHz, CDCl$_3$) δ 148.5, 131.0, 128.3, 122.6, 121.7, 110.8, 101.9, 33.3, 27.8, 27.3, 19.1 ppm.
Catalyst 11a was prepared according to the method reported in Angew. Chem. Int. Ed. 2009, 48, 5345.

EXAMPLE 23

Preparation of Chiral Bisphosphine Ligand (R,R,R)-La-(R,R,R)-Li

The reaction route for preparing (R,R,R)-La was described as below.

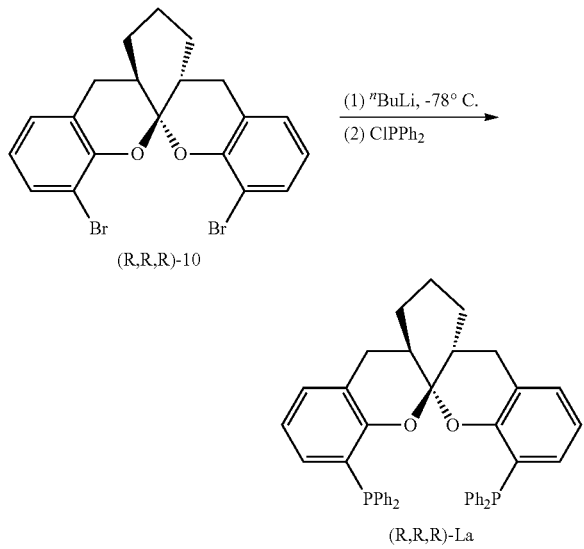

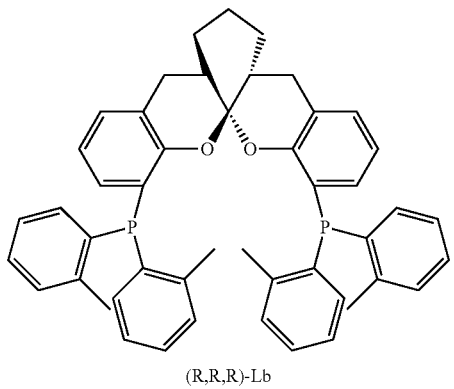

The substrate (R,R,R)-10 (175 mg, 0.389 mmol) and anhydrous tetrahydrofuran (4 mL) were added to 10 mL water-free and oxygen-free schlenk tube and cooled to less than −78° C. n-butyllithium (0.39 mL, 2.5 M in hexane, 0.972 mmol) was slowly added dropwise and the reaction mixture was stirred at −78° C. for 0.5 hr. Chlorodiphenylphosphine (0.18 mL, 0.972 mmol) was slowly added dropwise. Upon addition, the temperature was naturally raised to room temperature. The reaction mixture was stirred at room temperature for 10 hrs and then 10 mL distilled water was added to quench the reaction. The reaction mixture was extraced with dichloromethane (3×10 mL), and the organic phase was dried on anhydrous sodium sulfate and filtered and concentrated. The residue was purified by column chromatography to obtain target product (R,R,R)-La (187 mg, 73% yield).

(R,R,R)-La, white solid. Mp 101-103° C., $[\alpha]_D^{20}$=+113.4 (c 1.00, CHCl$_3$). $^1$H NMR (400 MHz, CDCl$_3$) δ 7.30-7.26 (m, 20H), 6.89 (d, J=7.2 Hz, 2H), 6.74 (t, J=7.2 Hz, 2H), 6.53-6.50 (m, 2H), 2.34-2.30 (m, 4H), 1.95-1.92 (m, 2H), 1.30-1.29 (m, 2H), 1.17-1.15 (m, 4H) ppm; $^{13}$C NMR (100 MHz, CDCl$_3$) δ 153.1 (d, J$_{(P,C)}$=14.2 Hz), 137.1 (d, J$_{(P,C)}$=11.8 Hz), 136.7 (d, J$_{(P,C)}$=10.9 Hz), 134.2 (d, J$_{(P,C)}$=21.9 Hz), 133.9 (d, J$_{(P,C)}$=20.2 Hz), 130.9 (d, J$_{(P,C)}$=3.2 Hz), 129.9 (s), 128.5 (s), 128.2-128.1 (m), 124.9 (d, J$_{(P,C)}$=14.1 Hz), 120.4-120.3 (m), 101.3, 33.5, 27.6, 26.7, 19.4 ppm; $^{31}$P (162 MHz, CDCl$_3$) δ −15.8 (s) ppm.

Chiral aromatic spiroketal bisphosphine ligand (R,R,R)-Lb can be prepared by the same method except that chlorodiphenylphosphine was replaced by chlorodi(o-tolyl)phosphine.

(R,R,R)-Lb, white solid, 40% yield. Mp 125-127° C., $[\alpha]_D^{20}$=+143.5 (c 1.00, CHCl$_3$). $^1$H NMR (400 MHz, CDCl$_3$) δ=7.24-7.12 (m, 8H), 7.05 (t, J=7.2 Hz, 4H), 6.88-6.85 (m, 4H), 6.79-6.72 (m, 4H), 6.53-6.50 (m, 2H), 2.39 (s, 6H), 2.34-2.23 (m, 2H), 2.18 (s, 6H), 1.99-1.95 (m, 2H), 1.34-1.15 (m, 8H) ppm; $^{13}$C NMR (75 MHz, CDCl$_3$) δ 153.5 (d, J$_{(P,C)}$=15.2 Hz), 143.2 (d, J$_{(P,C)}$=28.3 Hz), 142.7 (d, J$_{(P,C)}$=25.9 Hz), 135.3 (d, J$_{(P,C)}$=11.4 Hz), 134.9 (d, J$_{(P,C)}$=13.8 Hz), 133.5 (d, J$_{(P,C)}$=40.1 Hz), 131.0 (d, J$_{(P,C)}$=2.9 Hz), 130.0-129.6 (m), 128.3 (d, J$_{(P,C)}$=15.8 Hz), 125.8 (d, J$_{(P,C)}$=24.0 Hz), 123.3 (d, J$_{(P,C)}$=12.7 Hz), 120.6-120.5 (m), 101.4, 33.3, 27.7, 26.6, 21.2 (d, J$_{(P,C)}$=21.1 Hz), 21.0 (d, J$_{(P,C)}$=23.7 Hz), 19.3 ppm; $^{31}$P (121 MHz, CDCl$_3$) δ −33.4 ppm.

Chiral aromatic spiroketal bisphosphine ligand (R,R,R)-Lc can be prepared by the same method except that chlorodiphenylphosphine was replaced by chlorobis(3,5-dimethylphenyl)phosphine.

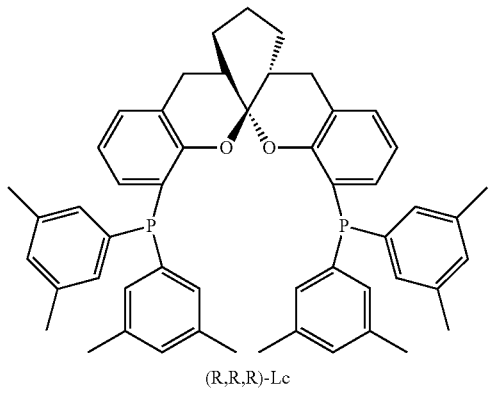

(R,R,R)-Lc, white solid, 70% yield. Mp 102-103° C., $[\alpha]_D^{20}$=+166.5 (c 1.00, CHCl$_3$). $^1$H NMR (300 MHz, CDCl$_3$) δ=6.93-6.84 (m, 14H), 6.73 (t, J=6.9 Hz, 2H), 6.47 (t, J=4.8 Hz, 2H), 2.45-2.38 (m, 4H), 2.24 (s, 12H), 2.21 (s, 12H), 2.04-1.97 (m, 2H), 1.30-1.26 (m, 2H), 1.12-1.07 (m, 4H) ppm; $^{13}$C NMR (75 MHz, CDCl$_3$) δ=153.1 (d, J$_{(P,C)}$=14.7 Hz), 137.3 (d, J$_{(P,C)}$=7.4 Hz), 137.2 (d, J$_{(P,C)}$=7.8 Hz), 136.9 (d, J$_{(P,C)}$=10.2 Hz), 136.5 (d, J$_{(P,C)}$=10.9 Hz), 132.1 (s), 131.8 (s), 131.5 (s), 130.8 (d, J$_{(P,C)}$=1.5 Hz), 130.2 (s), 129.8 (d, J$_{(P,C)}$=41.7 Hz), 125.5 (d, J$_{(P,C)}$=14.2 Hz), 120.1 (s), 120.1 (d, J$_{(P,C)}$=1.7 Hz), 101.1, 33.4, 27.3, 26.7, 21.3, 21.2, 19.5 ppm; $^{31}$P (121 MHz, CDCl$_3$) δ −15.2 ppm.

Chiral aromatic spiroketal bisphosphine ligand (R,R,R)-Ld can be prepared by the same method except that chlorodiphenylphosphine was replaced by chlorobis(3,5-di-tert-butylphenyl)phosphine.

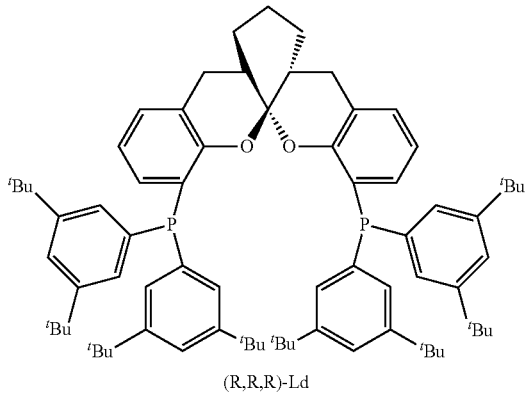

(R,R,R)-Ld (R,R,R)-Ld, white solid, 45% yield. Mp 100-101° C., $[\alpha]_D^{20}$=+140.5 (c 1.00, CHCl$_3$). $^1$H NMR (400 MHz, CDCl$_3$) δ=6.91-6.82 (m, 14H), 6.69 (t, J=6.6 Hz, 2H), 6.37 (t, J=5.0 Hz, 2H), 2.41-2.32 (m, 4H), 2.28 (s, 36H), 2.15 (s, 36H), 2.10-1.97 (m, 2H), 1.30-1.28 (m, 2H), 1.11-1.09 (m, 4H) ppm; $^{13}$C NMR (100 MHz, CDCl$_3$) δ=155.1 (d, J$_{(P,C)}$=15.0 Hz), 139.5 (d, J$_{(P,C)}$=8.4 Hz), 137.7 (d, J$_{(P,C)}$=8.0 Hz), 136.1 (d, J$_{(P,C)}$=10.8 Hz), 135.4 (d, J$_{(P,C)}$=11.2 Hz), 133.4 (s), 131.8 (s), 130.9 (s), 130.8 (d, J$_{(P,C)}$=12.0 Hz), 130.4 (s), 129.6 (d, J$_{(P,C)}$=42.2 Hz), 126.5 (d, J$_{(P,C)}$=16.2 Hz), 120.9 (s), 120.4 (d, J$_{(P,C)}$=2.2 Hz), 99.1, 33.4, 29.8, 27.3, 26.7, 25.6, 21.3, 21.2, 19.5 ppm; $^{31}$P (121 MHz, CDCl$_3$) δ –17.8 ppm.

Chiral aromatic spiroketal bisphosphine ligand (R,R,R)-Le can be prepared by the same method except that chlorodiphenylphosphine was replaced by chlorodi(p-tolyl)phosphine.

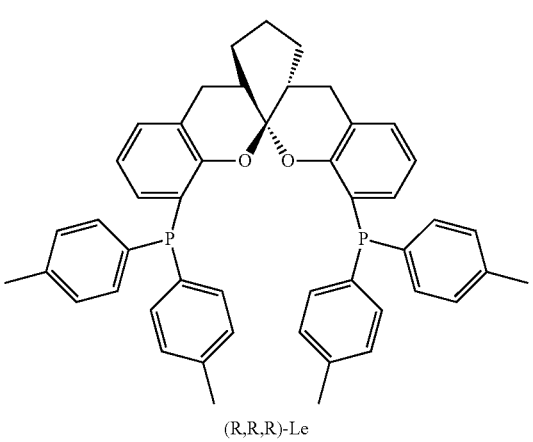

(R,R,R)-Le (R,R,R)-Le, white solid, 67% yield. Mp 90-92° C., $[\alpha]_D^{20}$=+118.5 (c 1.00, CHCl$_3$). $^1$H NMR (400 MHz, CDCl$_3$) δ=7.21-7.14 (m, 8H), 7.10-7.07 (m, 8H), 6.87 (d, J=7.2 Hz, 2H), 6.73 (t, J=7.6 Hz, 2H), 6.54 (t, J=5.6 Hz, 2H), 2.36-2.25 (m, 16H), 1.96-1.92 (m, 2H), 1.32-1.26 (m, 2H), 1.19-1.15 (m, 4H) ppm; $^{13}$C NMR (100 MHz, CDCl$_3$) δ=153.1 (d, J$_{(P,C)}$=14.5 Hz), 138.2 (s), 137.8 (s), 134.3-133.8 (m), 133.4 (d, J$_{(P,C)}$=10.4 Hz), 130.8 (d, J$_{(P,C)}$=2.6 Hz), 129.7 (s), 129.0-128.9 (m), 125.5 (d, J$_{(P,C)}$=14.0 Hz), 120.3-120.2 (m), 101.2, 33.4, 27.6, 26.7, 21.3, 19.4 ppm; $^{31}$P NMR (162 MHz, CDCl$_3$) δ –17.9 ppm.

Chiral aromatic spiroketal bisphosphine ligand (R,R,R)-Lf can be prepared by the same method except that chlorodiphenylphosphine was replaced by chlorodi(p-fluorophenyl)phosphine.

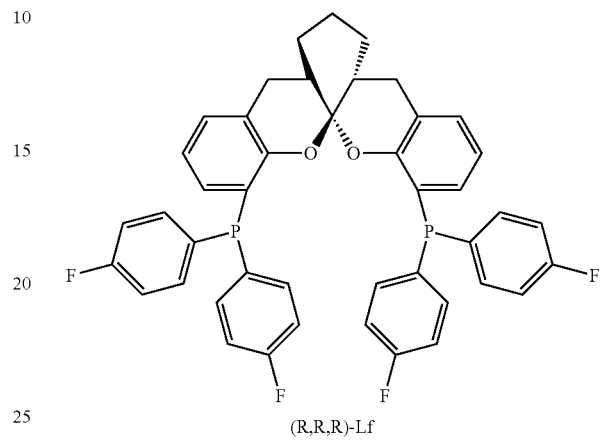

(R,R,R)-Lf (R,R,R)-Lf, white solid, 80% yield. Mp 76-77° C., $[\alpha]_D^{20}$=+88.0 (c 1.00, CHCl$_3$). $^1$H NMR (400 MHz, CDCl$_3$) δ=7.27-7.20 (m, 8H), 6.99-6.93 (m, 10H), 6.76 (t, J=7.6 Hz, 2H), 6.49-6.46 (m, 2H), 2.50-2.39 (m, 4H), 2.01-1.94 (m, 2H), 1.33-1.32 (m, 2H), 1.20-1.11 (m, 4H) ppm; $^{31}$P NMR (162 MHz, CDCl$_3$) δ –17.8 ppm; $^{19}$F NMR (376 MHz, CDCl$_3$) δ –112.3, –112.5 ppm.

Chiral aromatic spiroketal bisphosphine ligand (R,R,R)-Lg can be prepared by the same method except that chlorodiphenylphosphine was replaced by chlorodi(p-methoxylphenyl)phosphine.

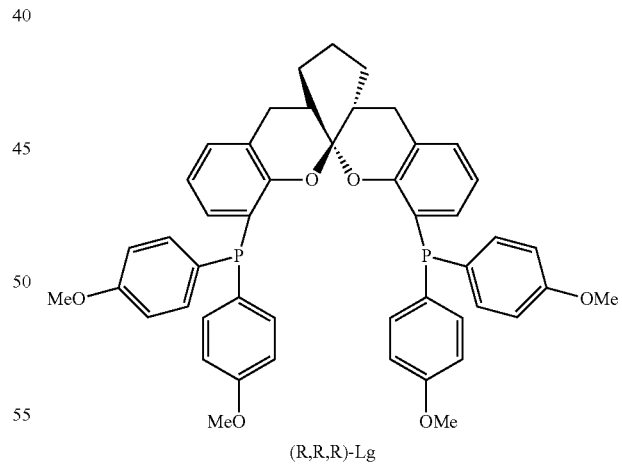

(R,R,R)-Lg (R,R,R)-Lg, white solid, 65% yield. Mp 91-92° C., $[\alpha]_D^{20}$=+122.5 (c 1.00, CHCl$_3$). $^1$H NMR (400 MHz, CDCl$_3$) δ=7.26-7.19 (m, 8H), 6.88-6.87 (m, 2H), 6.84-6.81 (m, 8H), 6.73 (t, J=7.2 Hz, 2H), 6.51 (t, J=5.2 Hz, 2H), 3.75 (s, 6H), 3.71 (s, 6H), 2.35-2.31 (m, 4H), 1.94-1.91 (m, 2H), 1.31-1.26 (m, 3H), 1.20-1.16 (m, 3H) ppm; $^{13}$C NMR (100 MHz, CDCl$_3$) δ=159.8 (d, J$_{(P,C)}$=38.8 Hz), 152.8 (d, J$_{(P,C)}$=13.9 Hz), 135.5-135.0 (m), 130.4 (s), 129.5 (s), 128.3 (d, J$_{(P,C)}$=8.1 Hz), 127.6 (d, J$_{(P,C)}$=9.0 Hz), 125.8 (d, $J_{(P,C)}$=13.3 Hz), 120.1 (d, $J_{(P,C)}$=1.6 Hz), 113.8-113.7 (m), 101.0, 55.0, 54.9, 33.4, 27.6, 26.6, 19.3 ppm; $^{31}$P NMR (162 MHz, CDCl$_3$) δ −18.8 ppm.

Chiral aromatic spiroketal bisphosphine ligand (R,R,R)-Lh can be prepared by the same method except that chlorodiphenylphosphine was replaced by chlorodicyclohexylphosphine.

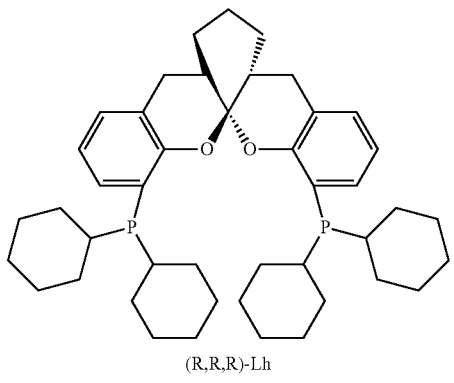

(R,R,R)-Lh (R,R,R)-Lh, white solid, 55% yield. Mp 95-96° C., $[\alpha]_D^{20}$=+88.5 (c 1.00, CHCl$_3$). $^1$H NMR (400 MHz, CDCl$_3$) δ=7.21-7.15 (m, 4H), 6.89-6.85 (m, 2H), 2.39-2.30 (m, 8H), 1.98-1.87 (m, 6H), 1.30-1.25 (m, 18H), 1.23-1.14 (m, 20 H) ppm; $^{31}$P NMR (162 MHz, CDCl$_3$) δ −21.6 ppm.

Chiral aromatic spiroketal bisphosphine ligand (R,R,R)-Li can be prepared by the same method except that chlorodiphenylphosphine was replaced by di-tert-butylchlorophosphine.

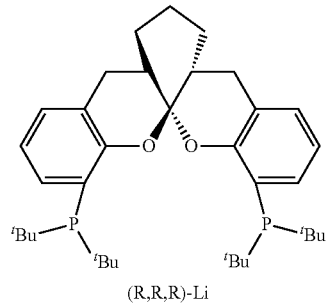

(R,R,R)-Li (R,R,R)-Li, white solid, 81% yield. $[\alpha]_D^{20}$=+78.1 (c 1.00, CHCl$_3$). $^1$H NMR (400 MHz, CDCl$_3$) δ=7.28-7.21 (m, 2H), 6.99-6.81 (m, 4H), 2.38-2.21 (m, 4H), 1.98-1.88 (m, 6H), 1.66-1.45 (m, 14H), 1.30-1.29 (m, 8H), 1.17-1.15 (m, 16H) ppm; $^{31}$P NMR (162 MHz, CDCl$_3$) δ −22.8 ppm.

EXAMPLE 24

Preparation of Compound (S,S,S)-10

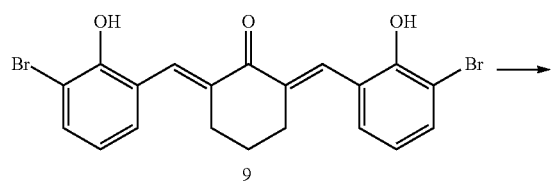

9

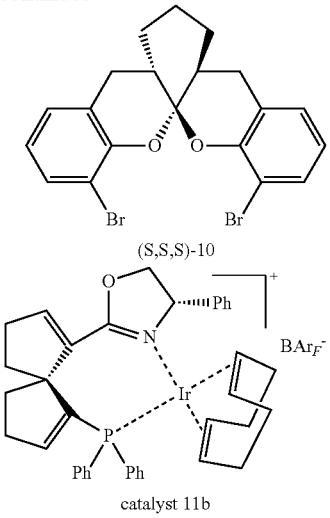

(S,S,S)-10 catalyst 11b

Chiral aromatic spiroketal compound (S,S,S)-10 was prepared by using compound 9 prepared in example 21 as hydrogenation substrate and compound 11b as catalyst. The reaction was conducted as follows: 9 (464 mg, 1 mmol), catalyst 11b (1.6 mg, 0.001 mmol) and 20 mL of anhydrous dichloromethane were added to a hydrogenation flask. The hydrogenation flask was placed in glovebox and transferred to a high pressure reactor. Hydrogen displacement was performed for three times, and then the reactor was charged with 50 atm of hydrogen. The reaction was carried out at room temperature for 24 hrs. After hydrogen was discharged, the reactor was opened and the solvent was removed under reduced pressure. The residue was separated by column chromatography to obtain (S,S,S)-10 with >99% ee in 91% yield.

Catalyst 11b was prepared according to the method reported in Angew. Chem. Int. Ed. 2009, 48, 5345.

(S,S,S)-10, white solid, $[\alpha]_D^{20}$=+86.1 (c 1.00, CHCl$_3$), >99% ee (determined by high performance liquid chromatography, chiral AD-H column, n-hexane/isobutyl alcohol=99:1, 0.5 mL/min, 230 nm; $t_R$ (minor)=11.87 min; $t_R$ (major)=14.10 min] $^1$H NMR (300 MHz, CDCl$_3$) δ 7.36 (dd, J=8.1, 0.9 Hz, 2H), 7.03 (dd, J=7.5, 0.6 Hz, 2H), 6.77 (t, J=7.5 Hz, 2H), 3.05 (dd, J=16.8, 6.3 Hz, 2H), 2.70 (dd, J=16.8 Hz, 7.2 Hz, 2H), 2.40-2.36 (m, 2H), 1.85-1.80 (m, 2H), 1.62-1.50 (m, 4H) ppm.

EXAMPLE 25

Preparation of Chiral Bisphosphine Ligand (S,S,S)-La-(S,S,S)-Li

Chiral bisphosphine ligand (S,S,S)-La-(S,S,S)-Li can be prepared according to the preparation method of example 23 except that (R,R,R)-10 was replaced by (S,S,S)-10. The NMR data of (S,S,S)-La-(S,S,S)-Li were the same as those of (R,R,R)-La-(R,R,R)-Li.

(S,S,S)-La, white solid, $[\alpha]_D^{20}$=−113.7 (c 1.00, CHCl$_3$);
(S,S,S)-Lb, white solid, $[\alpha]_D^{20}$=−145.5 (c 1.00, CHCl$_3$);
(S,S,S)-Lc, white solid, $[\alpha]_D^{20}$=−164.5 (c 1.00, CHCl$_3$);
(S,S,S)-Ld, white solid, $[\alpha]_D^{20}$=−145.2 (c 1.00, CHCl$_3$);
(S,S,S)-Le, white solid, $[\alpha]_D^{20}$=−117.6 (c 1.00, CHCl$_3$);
(S,S,S)-Lf, white solid, $[\alpha]_D^{20}$=−87.2 (c 1.00, CHCl$_3$);

(S,S,S)-Lg, white solid, $[\alpha]_D^{20}=-125.4$ (c 1.00, CHCl$_3$);
(S,S,S)-Lh, white solid, $[\alpha]_D^{20}=-85.1$ (c 1.00, CHCl$_3$);
(S,S,S)-Li, white solid, $[\alpha]_D^{20}=-78.3$ (c 1.00, CHCl$_3$).
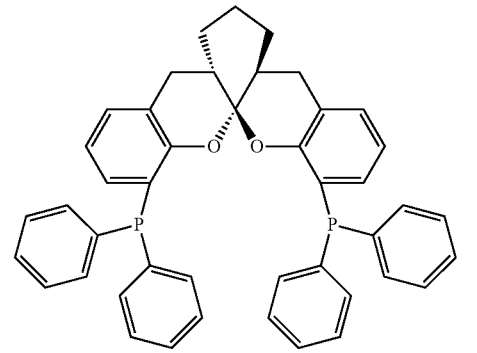
(S,S,S)-La
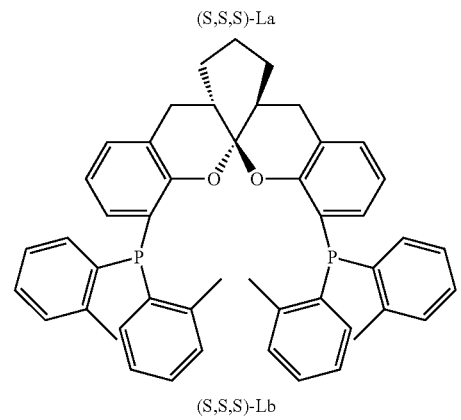
(S,S,S)-Lb
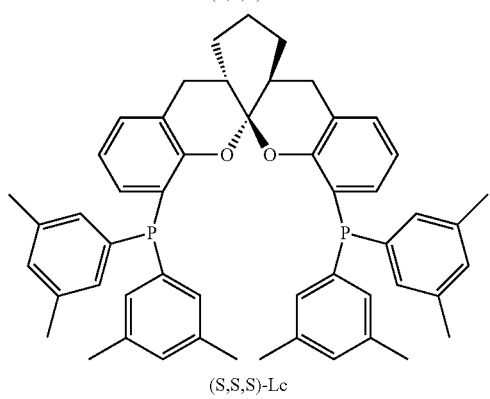
(S,S,S)-Lc
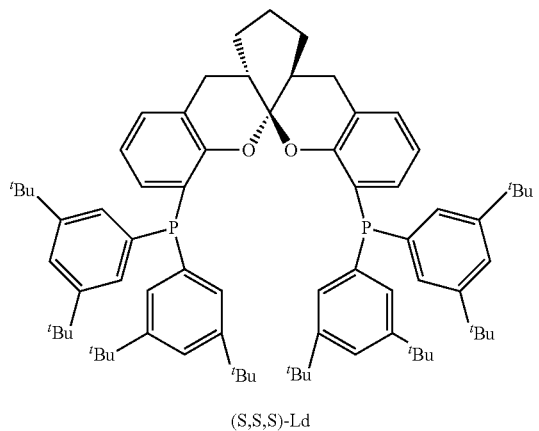
(S,S,S)-Ld
-continued
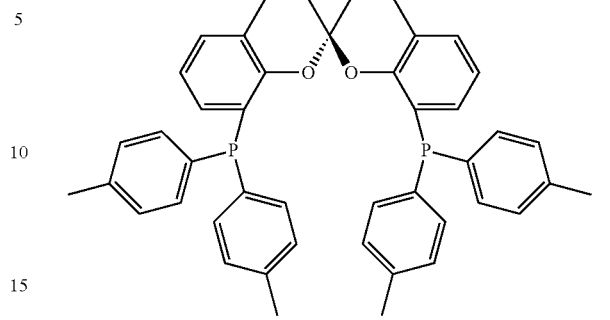
(S,S,S)-Le
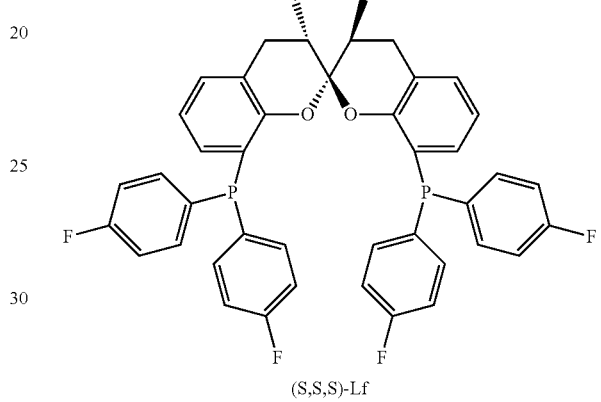
(S,S,S)-Lf
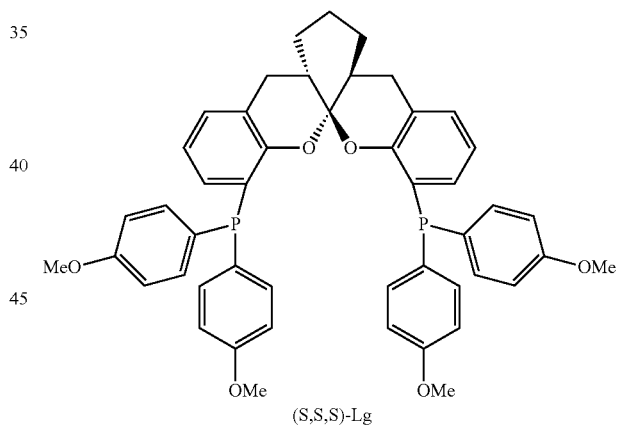
(S,S,S)-Lg
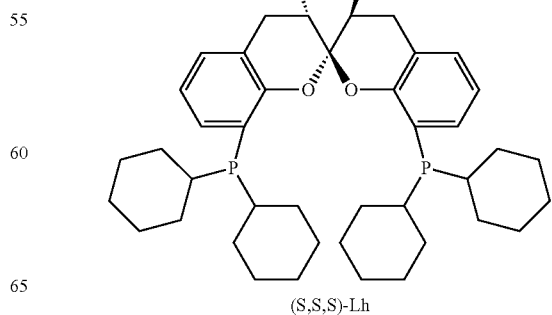
(S,S,S)-Lh

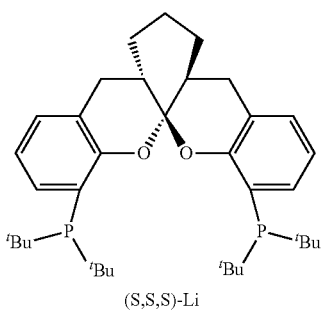

(S,S,S)-Li

EXAMPLE 26

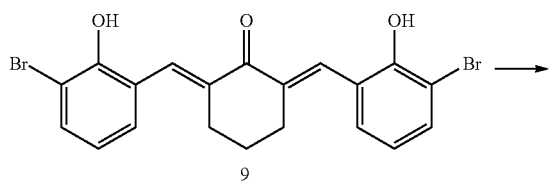

9

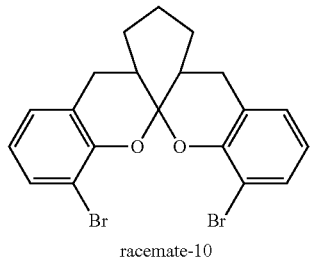

racemate-10

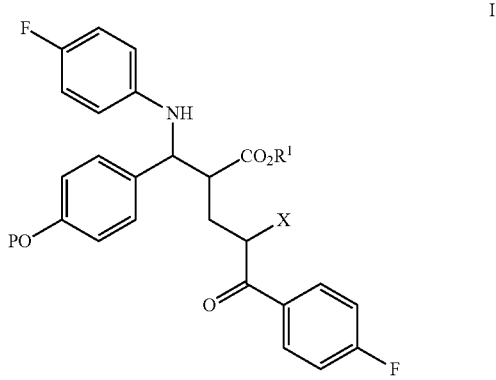

catalyst 11c

Racemic aromatic spiroketal compound 10 was prepared by using compound 9 prepared in example 21 as hydrogenation substrate and non-chiral compound 11 as catalyst. The reaction was conducted as follows: 3a (306 mg, 1 mmol), catalyst 11c (74 mg, 0.05 mmol) and 20 mL of anhydrous dichloromethane were added to a hydrogenation flask. The hydrogenation flask was placed in glovebox and transferred to a high pressure reactor. Hydrogen displacement was performed for three times, and then the reactor was charged with 50 atm of hydrogen. The reaction was carried out at room temperature for 24 hrs. After hydrogen was discharged, the reactor was opened and the solvent was removed under reduced pressure. The ratio of cis-form and trans-form of the product was determined by crude $^1$H-NMR. The residue was separated by column chromatography to obtain racemic compound 10 in 90% yield.

EXAMPLE 27

Preparation of Racemic Bisphosphine Ligand La-Li

The racemic bisphosphine ligand La-Li were respectively prepared according to the preparation method of Example 23 except that (R,R,R)-10 was replaced by racemic compound 10.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. A compound of formula I,

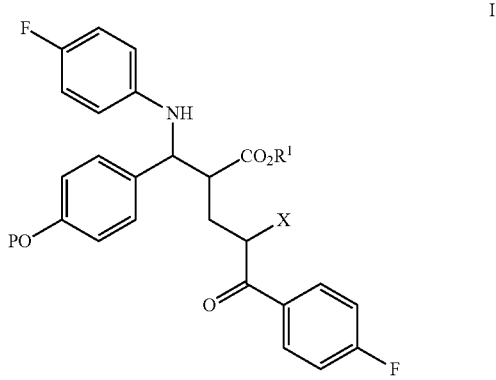

I wherein P is a hydrogen, an acetyl, a propionyl, a t-butyloxycarbonyl, a benzyl, a carbobenzoxy, a trityl, a trimethylsilyl, a tert-butyldimethylsilyl, a tert-butyldiphenylsilyl or a diphenylmethylsilyl;

$R^1$ is selected from the group consisting of: a hydrogen, a methyl, an ethyl, an isopropyl, an n-butyl, a tert-butyl, a benzyl, an allyl and an adamantyl;

X is H or $CO_2R^2$; and $R^2$ is selected from the group consisting of: a hydrogen, a methyl, an ethyl, an isopropyl, an n-butyl, a tert-butyl, a benzyl, an allyl and an adamantyl.

2. The compound of formula I of claim 1, wherein the compound of formula I is a compound of formula 4, or an enantiomer thereof,

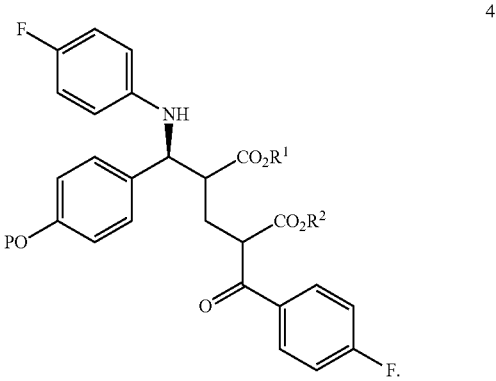

4

3. The compound of formula I of claim 1, wherein the compound of formula I is a compound of formula 5, or an enantiomer thereof,

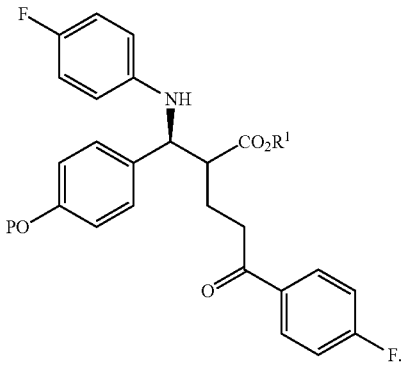

5

4. A preparation method for a compound of formula I,

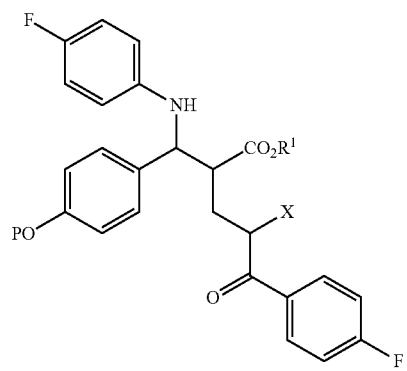

wherein the method comprises the following steps:
(a) subjecting a compound of formula 1 and p-fluoro aniline to an allyl amination reaction in the presence of a base to prepare a compound of formula 2;

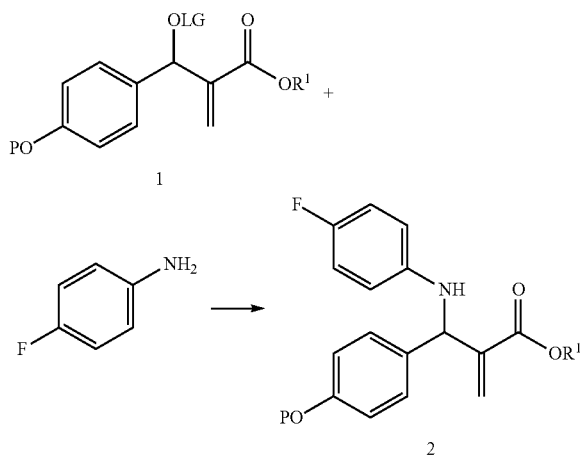

(b) subjecting the compound of formula 2 and a compound of formula 3 to an addition reaction under the action of a base to prepare the compound of formula I having a structure shown in formula 4A;

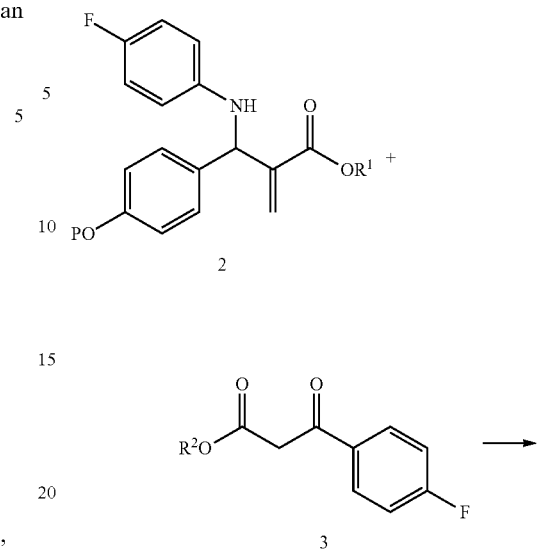

and optionally,
(c) removing an ester group at the β position of ketone carbonyl from the compound of formula I having a structure shown in formula 4A to form the compound of formula I having a structure shown in formula 5A,

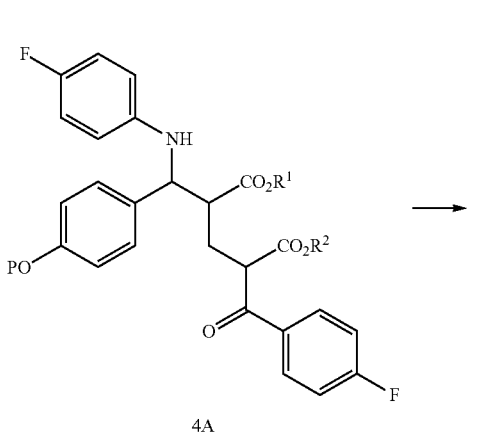

4A

-continued

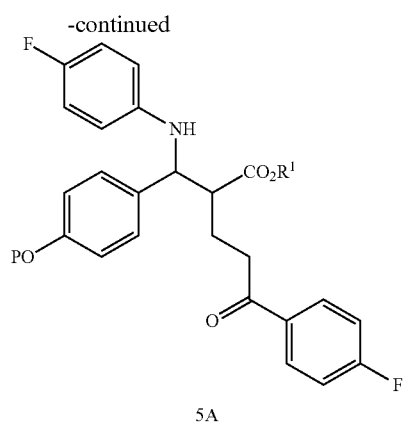

5A wherein P is a hydrogen, an acetyl, a propionyl, a t-butyloxycarbonyl, a benzyl, a carbobenzoxy, a trityl, a trimethylsilyl, a tert-butyldimethylsilyl, a tert-butyldiphenylsilyl or diphenylmethylsilyl;

X is H or $CO_2R^2$;

$R^1$ and $R^2$ are independently selected from the group consisting of: a hydrogen, a methyl, an ethyl, an isopropyl, an n-butyl, a tert-butyl, a benzyl, an allyl and an adamantyl; and LG is selected from the group consisting of an acetyl, a t-butyloxycarbonyl, a methoxycarbonyl, and a di(ethoxy)phosphinyl.

5. The method of claim 4, wherein a complex formed from a phosphine ligand and a transition metal catalyst precursor is used as a catalyst in step (a), wherein the phosphine ligand is

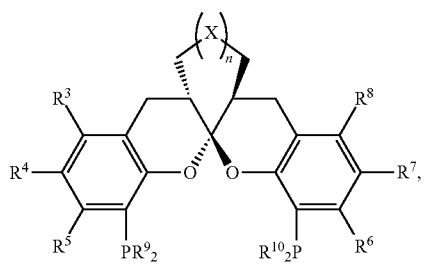

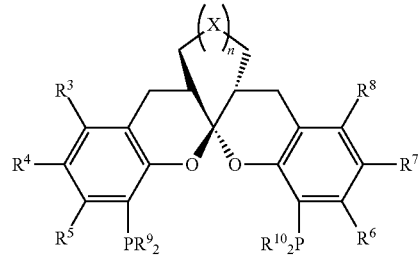

or a racemate thereof, wherein $R^3$, $R^4$, $R^5$, $R^6$, $R^7$ and $R^8$ are independently selected from the group consisting of a hydrogen, a halogen, and a substituted or unsubstituted group selected from the group consisting of: a $C_1$-$C_{10}$ alkyl, a $C_1$-$C_4$ alkoxy, a $C_3$-$C_{30}$ cycloalkyl and an aryl;

$R^9$ and $R^{10}$ are independently selected from the group consisting of a $C_3$-$C_{30}$ cycloalkyl, a $C_1$-$C_{10}$ alkyl, a 2-furyl and an aryl;

X is $CH_2$, NH, $NCH_3$, O or S;

n=an integer of 0-4;

said substitution refers to being substituted by a substituent which is selected from the group consisting of: a halogen, a $C_{1-6}$ alkyl, a $C_{1-6}$ haloalkyl and a $C_{1-6}$ alkoxy;

said transition metal catalyst precursor is a palladium catalyst precursor, and the palladium catalyst precursor is at least one selected from the group consisting of: $Pd(OAc)_2$, $PdCl_2$, $Pd_2(dba)_3$, $Pd_2(dba)_3 \cdot CHCl_3$, $Pd(dba)_2$, $[Pd(C_3H_5)Cl]_2$, $Pd(PPh_3)_4$, $Pd(PPh_3)_2Cl_2$, and $Pd(CH_3CN)Cl_2$.

6. The method of claim 4, wherein the base in step (a) is at least one selected from the group consisting of: potassium carbonate, potassium phosphate, cesium carbonate, triethylamine, diisopropylethylamine, N,O-bis(trimethylsilyl)acetamide, and tetra-n-butylammonium difluorotriphenylsilicate; and/or the base in step (b) is at least one selected from the group consisting of: 1,8-diazabicyclo[5.4.0]undec-7-ene, 1,4-diazabicyclo[2.2.2]octane, triethylamine, sodium hydroxide, potassium hydroxide, sodium hydride, potassium hydride, sodium ethoxide, and sodium methoxide.

7. A preparation method for a compound of formula 6A, wherein the method includes the step of subjecting the compound of formula I to a cyclization reaction under the action of a base to form the compound of formula 6A,

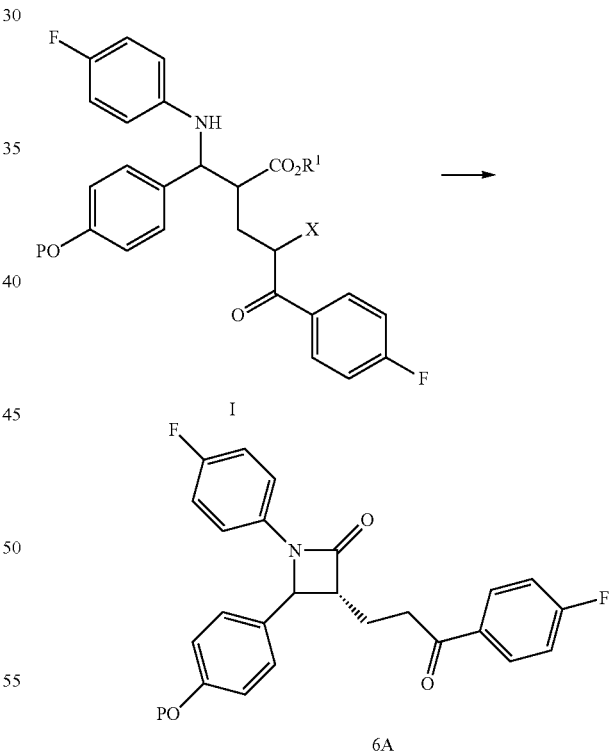

wherein P is a hydrogen, an acetyl, a propionyl, a t-butyloxycarbonyl, a benzyl, a carbobenzoxy, a trityl, a trimethylsilyl, a tert-butyldimethylsilyl or a diphenylmethylsilyl;

$R^1$ is a hydrogen, a methyl, an ethyl, an isopropyl, an n-butyl, a tert-butyl, a benzyl, an allyl or an adamantyl; and X is H.

8. A preparation method for Ezetimibe, which is a compound of formula 8, wherein the method includes the following steps:

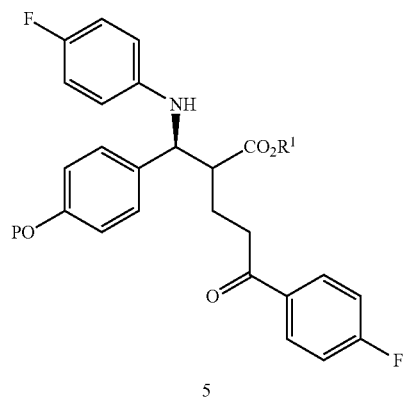

5

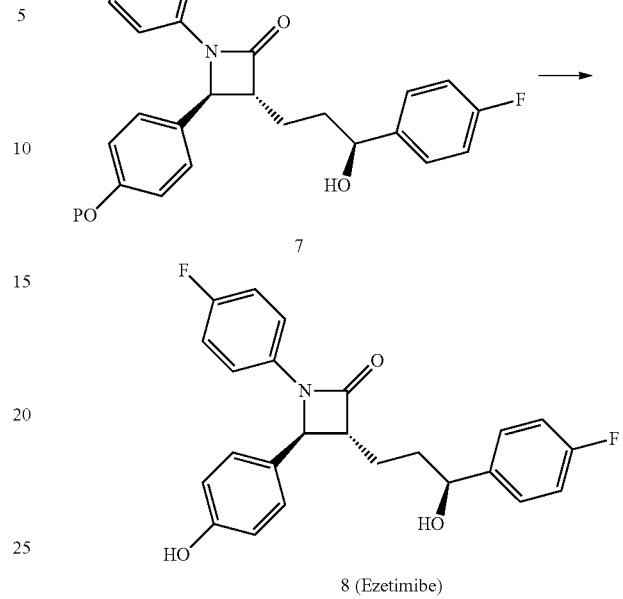

(i) subjecting a compound of formula 5 to a cyclization reaction under the action of a base to form a compound of formula 6;
(ii) subjecting the compound of formula 6 to an asymmetric reduction reaction at the position of ketone carbonyl in an organic solvent to obtain a compound of formula 7; and
(iii) removing a protecting group from the compound of formula 7 to obtain Ezetimibe, the compound of formula 8,

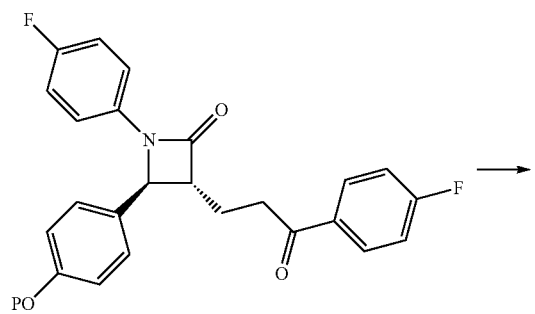

wherein P is a hydrogen, an acetyl, a propionyl, a t-butyloxycarbonyl, a benzyl, a carbobenzoxy, a trityl, a trimethylsilyl, a tert-butyldimethylsilyl or a diphenylmethylsilyl; and $R^1$ is a hydrogen, a methyl, an ethyl, an isopropyl, an n-butyl, a tert-butyl, a benzyl, an allyl or an adamantyl.

9. The preparation method of claim 8, wherein the organic solvent is at least one selected from the group consisting of benzene, toluene, xylene, dichloromethane, chloroform, carbon tetrachloride, 1,2-dichloroethane, diethyl ether, tetrahydrofuran, methanol, ethanol, N,N-dimethyl formamide and dimethyl sulfoxide.

10. The preparation method of claim 8, wherein the base is at least one selected from the group consisting of: bis(hexamethyldisilylamine) tin, lithium Hexamethyldisilazide, lithium diisopropylamide, butyllithium, tert-butyllithium, tert-butylmagnesium chloride, tert-butylmagnesium bromide, isopropylmagnesium chloride, and isopropylmagnesium bromide.

11. The method of claim 4, wherein the compound of formula 1 is prepared by a method including the following steps:

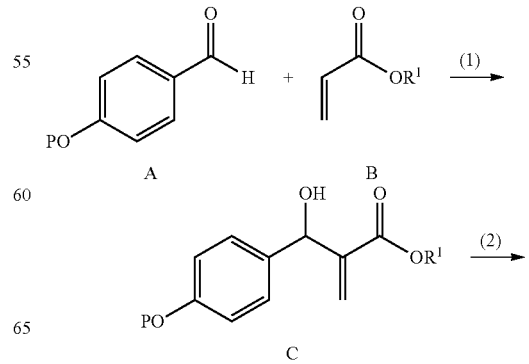

-continued

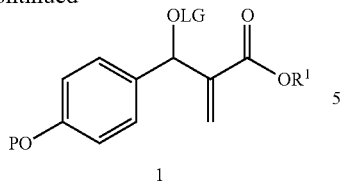

1

(1) subjecting a compound of formula A and a compound of formula B to a Morita-Baylis-Hillman reaction to prepare a compound of formula C; and
(2) protecting a hydroxyl on the compound of formula C to obtain the compound of formula 1,
wherein P is a hydrogen, an acetyl, a propionyl, a t-butyloxycarbonyl, a benzyl, a carbobenzoxy, a trityl, a trimethylsilyl, a tert-butyldimethylsilyl, or diphenylmethylsilyl;
$R^1$ is a hydrogen, a methyl, an ethyl, an isopropyl, an n-butyl, a tert-butyl, a benzyl, an allyl or an adamantyl; and
LG is an acetyl, a t-butyloxycarbonyl, a methoxycarbonyl, or a di(ethoxy)phosphinyl.

12. The preparation method of claim 7, wherein the base is at least one selected from the group consisting of: bis (hexamethyldisilylamine) tin, lithium Hexamethyldisilazide, lithium diisopropylamide, butyllithium, tert-butyllithium, tert-butylmagnesium chloride, tert-butylmagnesium bromide, isopropylmagnesium chloride, and isopropylmagnesium bromide.

\* \* \* \* \*